United States Patent
Trotti et al.

(10) Patent No.: US 11,369,596 B2
(45) Date of Patent: Jun. 28, 2022

(54) METHODS OF TREATING A NEURODEGENERATIVE DISEASE IN A MAMMAL IN NEED THEREOF

(71) Applicant: Thomas Jefferson University, Philadelphia, PA (US)

(72) Inventors: Davide Trotti, Bala Cynwyd, PA (US); Piera Pasinelli, Bala Cynwyd, PA (US); Michael R. Jablonski, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 16/289,273

(22) Filed: Feb. 28, 2019

(65) Prior Publication Data

US 2019/0192503 A1    Jun. 27, 2019

Related U.S. Application Data

(63) Continuation of application No. 15/103,234, filed as application No. PCT/US2014/069310 on Dec. 9, 2014, now Pat. No. 10,258,615.

(60) Provisional application No. 61/913,738, filed on Dec. 9, 2013.

(51) Int. Cl.
| | |
|---|---|
| *A61K 31/473* | (2006.01) |
| *A61K 45/06* | (2006.01) |
| *A61K 31/428* | (2006.01) |
| *A61K 31/4725* | (2006.01) |
| *A61K 31/496* | (2006.01) |
| *A61K 31/55* | (2006.01) |

(52) U.S. Cl.
CPC .......... *A61K 31/473* (2013.01); *A61K 31/428* (2013.01); *A61K 31/4725* (2013.01); *A61K 31/496* (2013.01); *A61K 31/55* (2013.01); *A61K 45/06* (2013.01)

(58) Field of Classification Search
CPC .............. A61K 31/428; A61K 31/4725; A61K 31/473; A61K 31/496; A61K 31/55; A61K 45/06; A61P 25/14; A61P 25/16; A61P 25/28
See application file for complete search history.

(56) References Cited

U.S. PATENT DOCUMENTS

| | | |
|---|---|---|
| 5,007,790 A | 4/1991 | Shell |
| 5,169,645 A | 8/1992 | Shukla et al. |
| 5,582,837 A | 10/1996 | Shell |
| 5,972,389 A | 10/1999 | Shell et al. |
| 6,340,475 B2 | 1/2002 | Shell et al. |
| 6,451,808 B1 | 9/2002 | Cowles |
| 6,488,962 B1 | 12/2002 | Berner et al. |
| 2002/0051820 A1 | 5/2002 | Shell et al. |
| 2003/0039688 A1 | 2/2003 | Shell et al. |
| 2003/0044466 A1 | 3/2003 | Markey et al. |
| 2003/0104053 A1 | 6/2003 | Gusler et al. |
| 2003/0104062 A1 | 6/2003 | Berner et al. |
| 2003/0147952 A1 | 8/2003 | Lim et al. |
| 2012/0077741 A1* | 3/2012 | Delfani .............. A61K 38/1858 514/8.1 |
| 2013/0116274 A1 | 5/2013 | Chen |
| 2014/0235631 A1 | 8/2014 | Bunt et al. |

FOREIGN PATENT DOCUMENTS

| | | |
|---|---|---|
| WO | 1990/011757 A1 | 10/1990 |
| WO | 1993/018755 A1 | 9/1993 |
| WO | 1997/047285 A1 | 12/1997 |
| WO | 1998/011879 A1 | 3/1998 |
| WO | 1998/055107 A1 | 12/1998 |
| WO | 2001/032217 A2 | 5/2001 |
| WO | 2001/056544 A2 | 8/2001 |
| WO | 2001/097783 A1 | 12/2001 |
| WO | 2002/032416 A2 | 4/2002 |
| WO | 2002/096404 A1 | 12/2002 |
| WO | 2003/035029 A1 | 5/2003 |
| WO | 2003/035039 A1 | 5/2003 |
| WO | 2003/035040 A1 | 5/2003 |
| WO | 2003/035041 A1 | 5/2003 |
| WO | 2003/035177 A2 | 5/2003 |

OTHER PUBLICATIONS

National Center for Biotechnology Information. "PubChem Compound Summary for CID 5479530, Ceftriaxone" PubChem, https://pubchem.ncbi.nlm.nih.gov/compound/Ceftriaxone. Accessed Aug. 15, 2020. Create: Aug. 1, 2005. (Year: 2005).*
Meadows et al., "Anti-VEGF Therapies in the Clinic", 2012, Cold Spring Harb. Perspect. Med., 2(10), pp. 1-27. (doi: 10.1101/cshperspect.a006577). (Year: 2012).*
Sieving et al., "Ciliary neurotrophic factor (CNTF) for human retinal degeneration: Phase I trial of CNTF delivered by encapsulated cell intraocular implants", 2006, PNAS (Proceedings of the National Academy of Sciences), 103(10), pp. 3896-3901. (doi/10.1073/pnas.0600236103) (Year: 2006).*

(Continued)

*Primary Examiner* — My-Chau T. Tran
(74) *Attorney, Agent, or Firm* — Riverside Law LLP

(57) ABSTRACT

The present invention provides a method of treating or ameliorating a neurodegenerative disease in a mammal, the method comprising administering to the mammal a therapeutically effective amount of a neurodegenerative disease drug, wherein the drug is a substrate of an ABC transporter inhibitor, wherein the mammal is further administered a therapeutically effective amount of an ABC transporter inhibitor, whereby the neurodegenerative disease is treated in the mammal. In certain embodiments, the neurodegenerative disease comprises at least one selected from the group consisting of spinal cord injury, Alzheimer's disease, Parkinson's disease, Huntington's disease, prion disease, amyotrophic lateral sclerosis, a tauopathy, and chronic traumatic encephalopathy.

16 Claims, 16 Drawing Sheets

(56) References Cited

OTHER PUBLICATIONS

Henriques et al., "Neurotrophic growth factors for the treatment of amyotrophic lateral sclerosis: where do we stand?", 2010, Frontiers in Neuroscience, 4(Article 32), pp. 1-14. (doi: 10.3389/fnins.2010.00032) (Year: 2010).*

Garbuzova-Davis et al., "Potential new complication in drug therapy development for amyotrophic lateral sclerosis", 2016, Expert Review of Neurotherapeutics, 16(12), pp. 1397-1405. (dx.doi.org/10.1080/14737175.2016.1207530) (Year: 2016).*

Ghasemi et al., "Ciliary neurotrophic factor (CNTF) delivery to retina: an overview of current research advancements", 2018, Artificial Cells, Nanomedicine, and Biotechnology, 46(8), pp. 1694-1707. (DOI: 10.1080/21691401.2017.1391820) (Year: 2018).*

Storkebaum et al., "Treatment of motoneuron degeneration by intracerebroventricular delivery of VEGF in a rat model of ALS", 2005, Nat. Neurosci., 8(1), pp. 85-92. (doi.org/10.1038/nn1360) (Year: 2005).*

Lambrechts et al., "VEGF at the neurovascular interface: Therapeutic implications for motor neuron disease", 2006, Biochimica et Biophysica Acta (BBA)—Molecular Basis of Disease, vol. 1762, Issues 11-12, pp. 1109-1121. (doi.org/10.1016/j.bbadis.2006.04.005) (Year: 2006).*

KeiferJr., "Gene and protein therapies utilizing VEGF for ALS", Mar. 2014 (Available online Oct. 29, 2013), Pharmacology & Therapeutics, vol. 141, Issue 3, pp. 261-271. (doi.org/10.1016/j.pharmthera.2013.10.009) (Year: 2014).*

Akhtar, et al., "The emerging role of P-glycoprotein inhibitors in drug delivery: a patent review". 2011, Expert Opinion on Therapeutic Patents, 21(4), pp. 561-576.

CDMRP: Congressionally Directed Medical Research Programs. Annual Report 1-108, Sep. 2013 [retrieved on Mar. 2, 2015]. Retrieved from the Internet. <URL: http://cdmrp.army.mil/pubs/annreports/2013annrep/2013annreport.pdf>, pp. 38-39.

Chou, T., et al., "Quantitative analysis of dose-effect relationships: the combined effects of multiple drugs on enzyme inhibitors", Adv. Enzyme Regul., vol. 22, pp. 27-55, 1984.

Holford, N.H., et al., "Understanding the dose-effect relationship: clinical application of pharmacokinetic-pharmacodynamic models", Clin. Pharmacokinet., vol. 6, pp. 429-453, 1981.

Jablonski, M.R., et al., Inhibiting drug efflux transporters improves efficacy of ALS therapeutics, Annals of Clinical and Translational Neurology, vol. 1, No. 12, pp. 996-1005, 2014.

Jablonski, M.R., et al., "Selective increase of two ABC drug efflux transporters at the blood spinal cord barrier suggests induced pharmacoresistance in ALS", Neurobiology of Disease, vol. 4, No. 2, pp. 194-200, 2012.

Jedlitschky, G., et al., "Structure and function of the MRP2 (ABCC2) protein and its role in drug disposition", Expert Opinion on Drug Metabolism & Toxicology, vol. 2, No. 3, pp. 351-366, 2006.

Li, J., et al., Electrophysiologic Biomarkers for Assessing Disease Progression and the Effect of Riluzole in SOD1 G93A ALS Mice, PLOS One, vol. 8, No. 6, e65976-1 to e65976-7, Jun. 2013. [retrieved on Apr. 2, 2015], Retrieved from the internet <URL: http://www.ncbi.nlm.nih.gov/pmc/articles/PMC3675066/>.

Loewe, S., et al., "Effect of combinations: mathematical basis of the problem", Arch. Exp. Pathol. Pharmacol., vol. 114, pp. 313-326, 1926.

Milane, et al., "Interactions between riluzole and ABCG2/BCRP transporter". 2009, Neuroscience Letters, 452(1), pp. 12-16.

Milane, et al., "P-glycoprotein expression and function are increased in an animal model of amyotrophic lateral sclerosis", 2010, Neuroscience Letters, 472(3), pp. 166-170.

Pasinelli, P., "Rethinking Drug Treatment Approaches in ALS by Targeting ABC Efflux Transporters", Internet, Oct. 2012, Retrieved from the Internet: URL.www.dtic.mil [retrieved on May 4, 2017].

Schinkel, et al., "Mammalian drug efflux transporters of the ATP binding cassette (ABC) family: an overview", 2003, Advanced Drug Delivery Reviews, 55(1), pp. 3-29.

Sharom, F.J., "ABC multidrug transporters: structure, function and role in chemoresistance", Pharmacogenomics, vol. 9, No. 1, pp. 105-127, 2008.

Szakacs, G., et al., "Targeting multidrug resistance in cancer", Nat. Rev. Drug Discov., vol. 5, No. 3, pp. 219-234, 2006.

European Supplementary Partial Search Report issued in corresponding European Application No. 14869548.9 dated Jun. 14, 2017.

National Center for Biotechnology Information. PubChem Compound Database; CID=5070, https://pubchem.ncbi.nlm.nih.gov/compound/5070 (accessed May 29, 2018) Create date: Mar. 25, 2005 . (Year: 2005).

National Center for Biotechnology Information. PubChem Compound Database; CID=119373, https://pubchem.ncbi.nlm.nih.gov/compound/119373 (accessed May 29, 2018) Create date: Aug. 8, 2005. (Year: 2005).

Extended European Search Report issued in European Patent Application No. 14869548.9 dated Sep. 18, 2017.

* cited by examiner

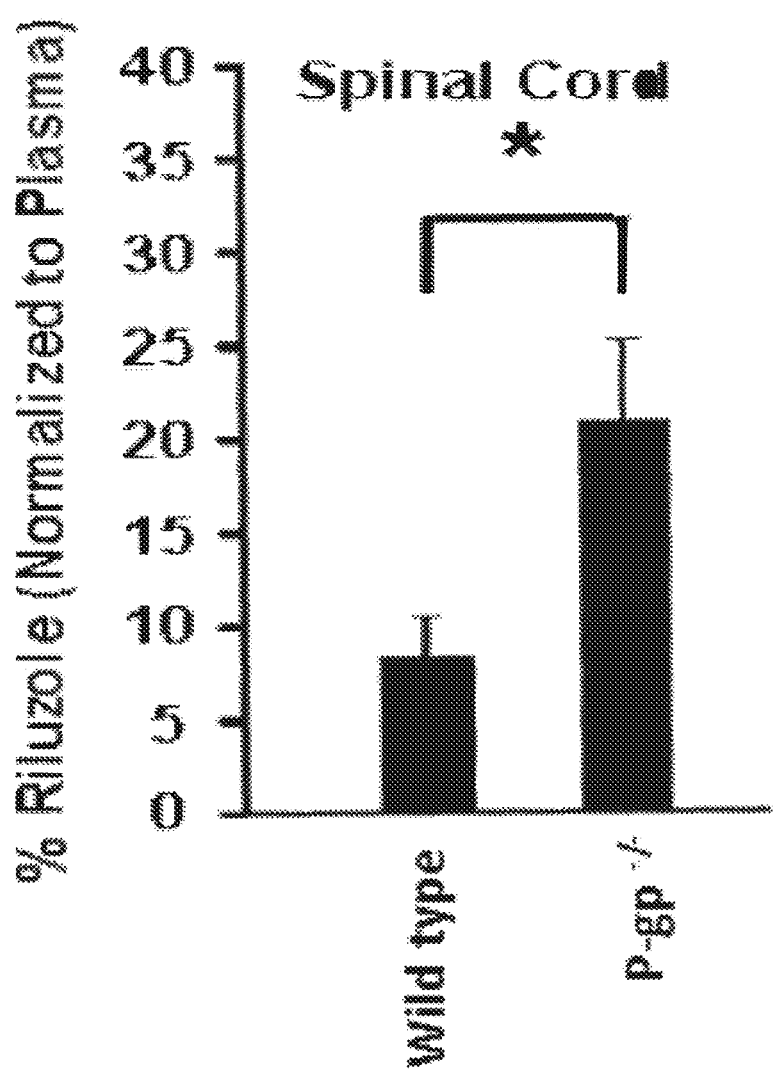

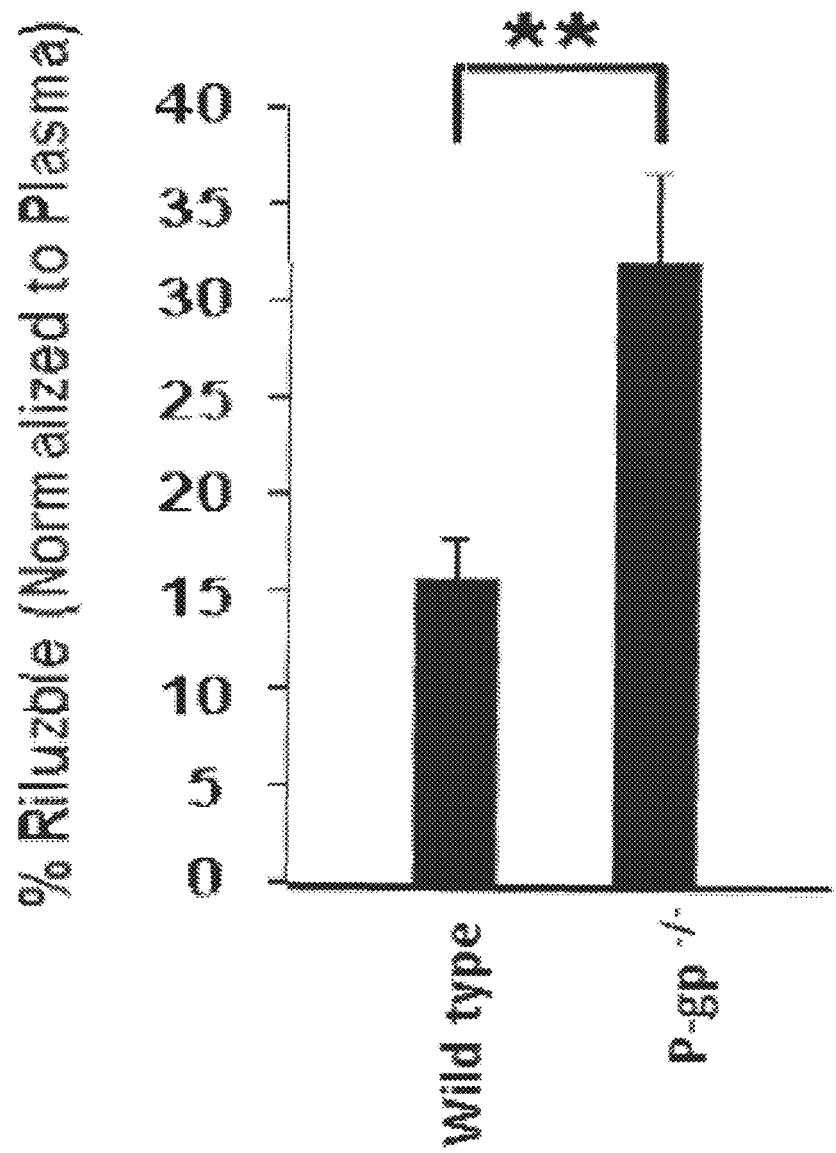

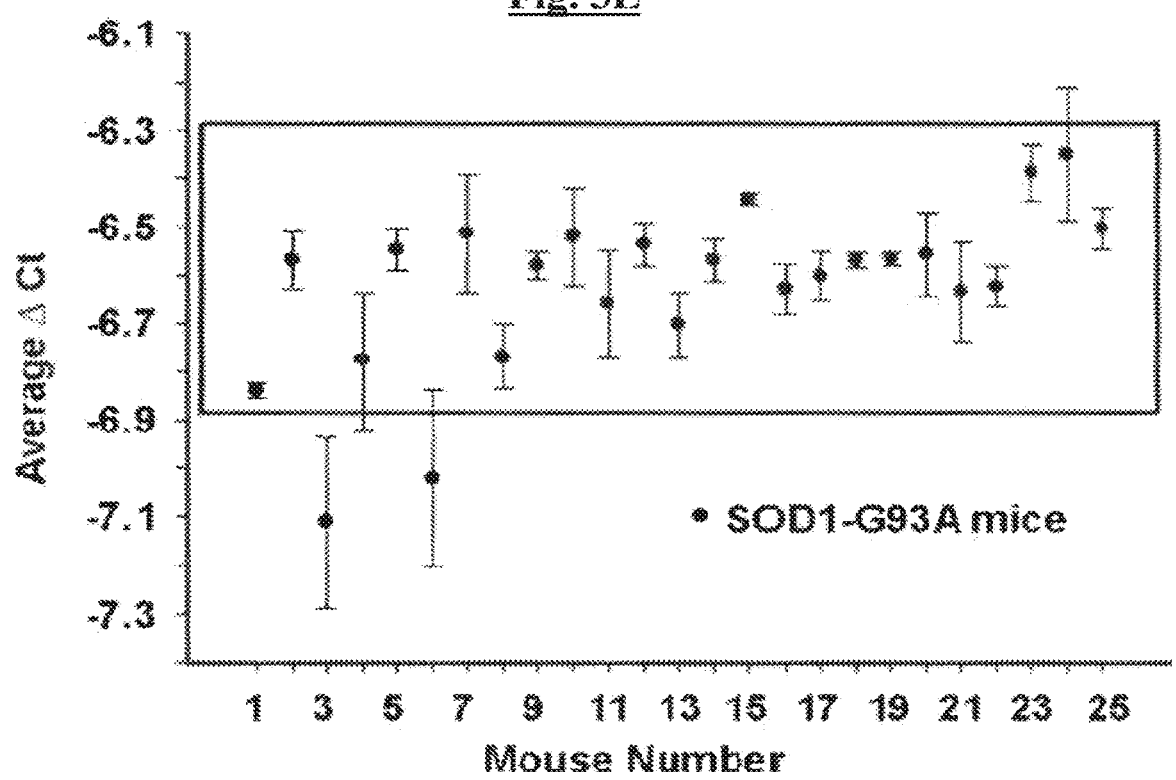

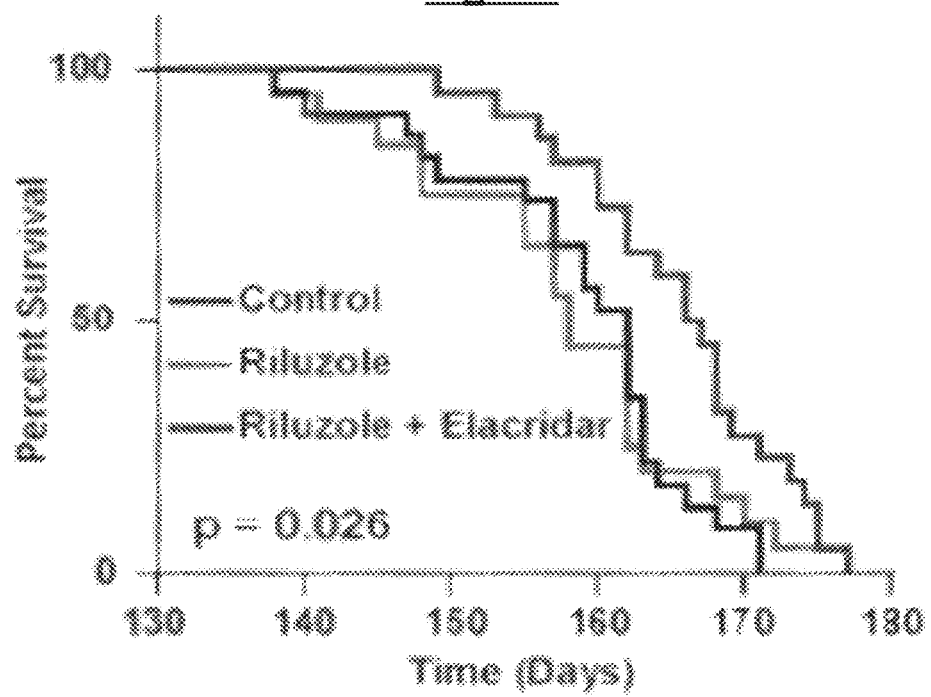
Fig. 4A
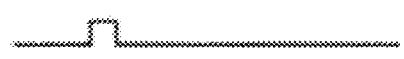
Fig. 4B
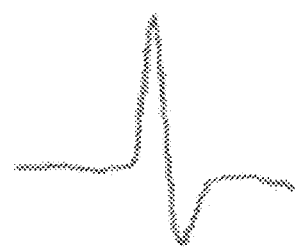
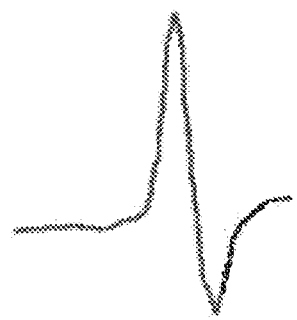

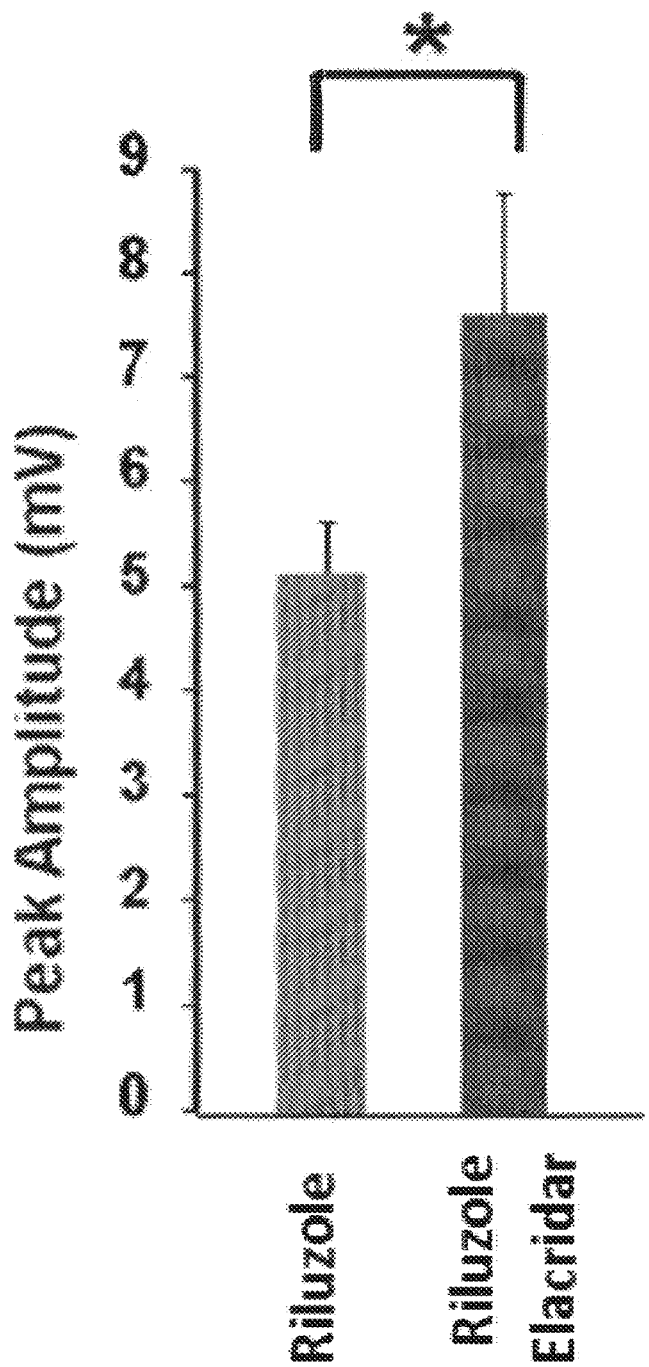

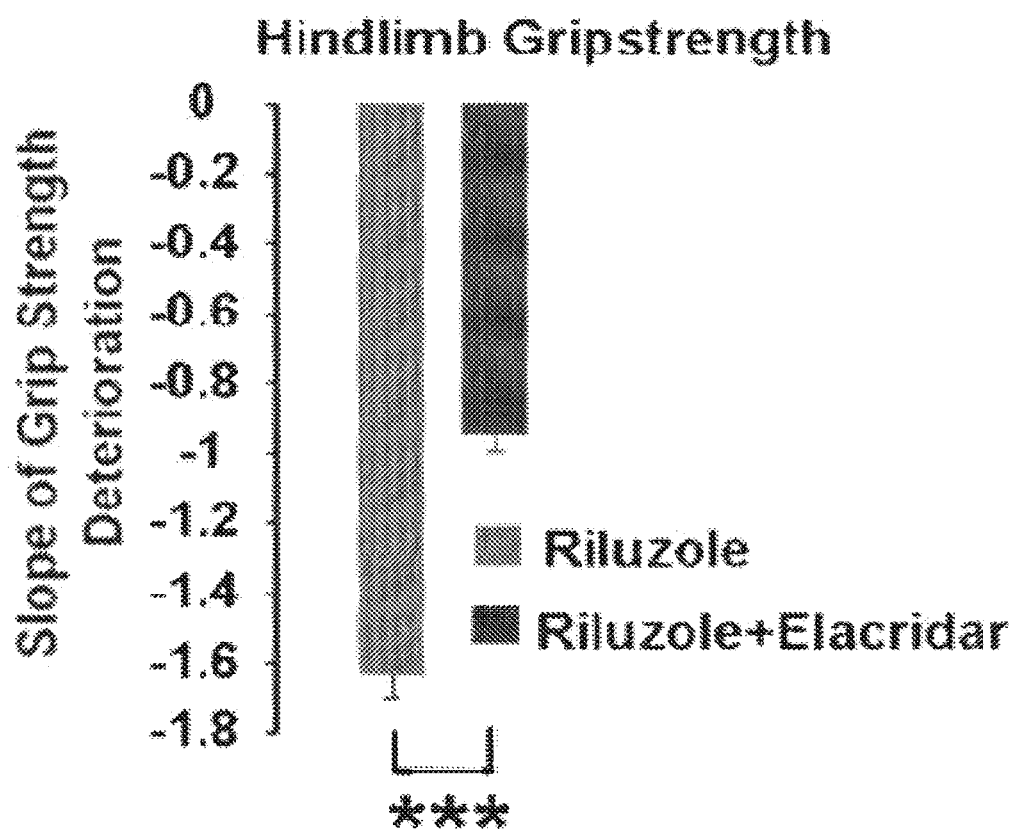

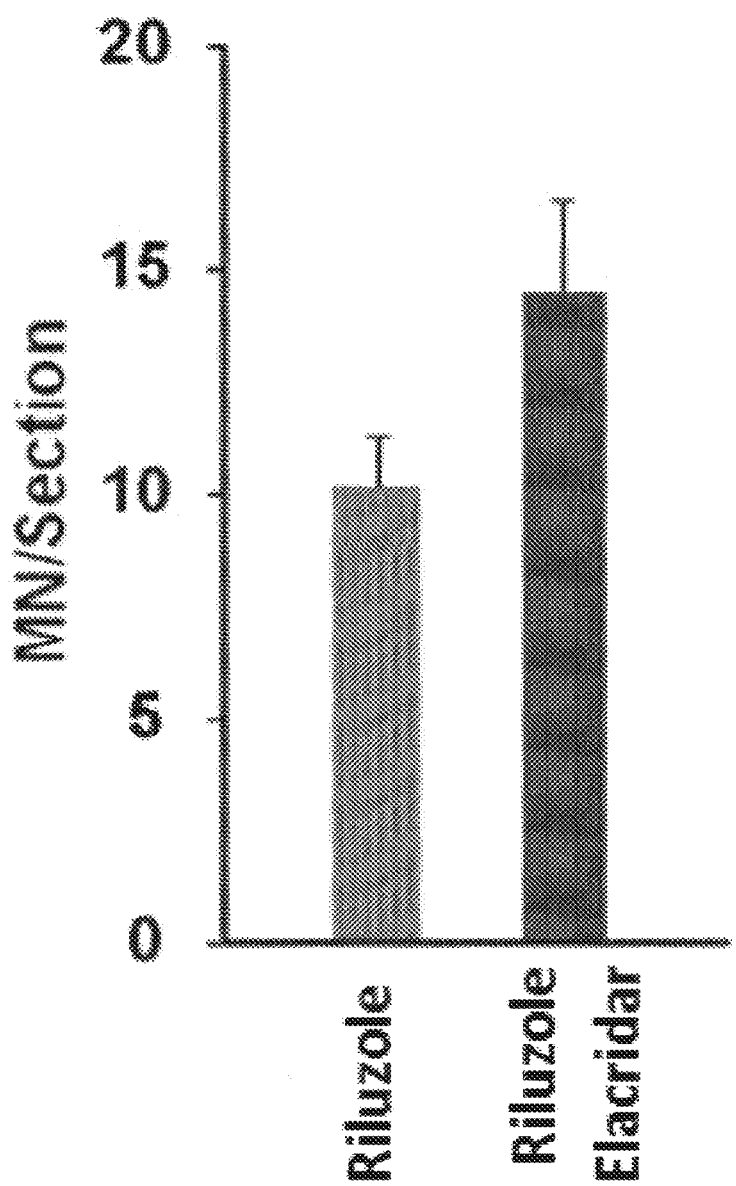

Riluzole　　　　　Riluzole+Elacridar

METHODS OF TREATING A NEURODEGENERATIVE DISEASE IN A MAMMAL IN NEED THEREOF

CROSS REFERENCE TO RELATED APPLICATIONS

This application is a U.S. Continuation Patent Application of U.S. patent Ser. No. 15/103,234, filed Jun. 9, 2016, published as US 2016-0303107 A1 on Oct. 20, 2016; which claims priority to International Patent Application No. PCT/US14/69310, filed on Dec. 9, 2014, published as WO 2015/089049 on Jun. 18, 2015; which claims priority to U.S. Provisional Application No. 61/913,738, filed on Dec. 9, 2013, which are incorporated herein by reference in their entirety.

STATEMENT REGARDING FEDERALLY SPONSORED RESEARCH OR DEVELOPMENT

This invention was made with government support under grant number AL100153 awarded by the U.S. Department of Defense and grant number RO1 NS74886 awarded by the National Institutes of Health. The government has certain rights in the invention.

BACKGROUND OF THE INVENTION

Amyotrophic lateral sclerosis (ALS), also known as Lou Gehrig's disease, is a debilitating disease with varied etiology. ALS is characterized by rapidly progressive weakness, muscle atrophy and fasciculations, muscle spasticity, difficulty speaking (i.e., dysarthria), difficulty swallowing (i.e., dysphagia) and difficulty breathing (i.e., dyspnea). Worldwide, ALS kills about 100,000 yearly, with 125,000 new ALS diagnoses yearly.

ALS causes muscle weakness and atrophy throughout the body due to the degeneration of the upper and lower motor neurons. Individuals affected by the disorder may ultimately lose the ability to initiate and control all voluntary movement, although bladder and bowel sphincters and the muscles responsible for eye movement are usually spared until the terminal stages of the disease. Most patients do not lose cognitive function, but about 5% develop frontotemporal dementia.

The precise cause of ALS is still unknown, but mutations in the gene that produces the Cu/Zn superoxide dismutase (SOD1) enzyme are present in approximately 20% of familial ALS cases. SOD1 is a powerful antioxidant that protects the body from damage caused by the toxic free radical superoxide, which is generated in the mitochondria. To date, over 110 different mutations in SOD1 have been linked with ALS. Failure of defenses against oxidative stress upregulates programmed cell death (apoptosis). An accumulation of free radicals due to faulty SOD1 functioning may thus lead to motor neuron degeneration. However, it is also possible that mutant SOD1 induces toxicity by a gain of function. For example, in some mutant SOD1 mice, mutant SOD1 aggregates (misfolded protein deposits) were found only in diseased tissues, and greater amounts were detected during motor neuron degeneration. This observation is consistent with a model where mutant SOD1 aggregates help disrupt cellular functions by damaging mitochondria, proteasomes or protein folding chaperones. In humans, SOD1 mutations cause only 2% of total ALS cases, and the etiological mechanisms may be distinct from those responsible for the sporadic form of the disease. For non-familial cases (around 90% of ALS cases), the disease may be triggered by head trauma, military service, or participation in contact sports.

Riluzole (RILUTEK®) is the only drug currently approved to treat ALS, but its therapeutic success is limited. Riluzole slows down disease progression by about 3-9 months, prolongs survival by several months, and delays the need for ventilation support. However, the drug does not reverse the damage already done to motor neurons, and may cause liver damage in about 10% of the patients.

In one aspect, development of effective ALS treatments may be hampered by a combination of low drug bioavailability and disease-driven pharmacoresistance, which limits CNS drug penetration and ultimately compromises drug efficacy.

Pharmacoresistance is mediated for example by the ATP-binding cassette ("ABC") drug efflux transporters. ABC transporters are transmembrane proteins that utilize the energy of adenosine triphosphate (ATP) hydrolysis to carry out biological processes, including translocation of substrates (e.g., metabolites, lipids, sterols and drugs) across extra- and intracellular membranes. ABC transporters play a crucial role in the development of multidrug resistance (MDR), whereby patients eventually develop resistance not only to the drug they are taking but also to additional types of drugs to which they had not been exposed. MDR is linked by the increased cellular excretion of the drug by ABC transporters. ABC transporter families include ABCB1 (also known as P-glycoprotein, P-gp or MDR1), which transports organic cationic compounds or neutral compounds; MRP, which transports organic anionic compounds; and ABCG2 (also known as breast cancer resistance protein or BCRP), which confers resistance to Topoisomerase I or II inhibitors such as topotecan, irinotecan, and doxorubicin. ABC transporters are predominantly located in the lumen of endothelial cells of the blood-brain barrier, where they limit the entry of neurotoxins into the CNS. Unfortunately, clinical trials in cancer patients to which ABC transporter inhibitors were co-administered, with the objective of increasing the anticancer drug efficacy, had ultimately disappointing outcomes (Sharom, 2008, Pharmacogenomics 9(1):105-127; Szakacs et al., 2006, Nat. Rev. Drug Discov. 5:219-234).

There is a need in the art for novel methods of treating neurodegenerative diseases in a mammal in need thereof. The present invention fulfills this need.

BRIEF SUMMARY OF THE INVENTION

The invention includes a pharmaceutical composition comprising a neurodegenerative disease drug and an ABC transporter inhibitor, wherein the drug is a substrate of an ABC transporter.

The inventor further includes a method of treating or ameliorating a neurodegenerative disease in a mammal in need thereof, the method comprising administering to the mammal a therapeutically effective amount of a neurodegenerative disease drug, wherein the drug is a substrate of an ABC transporter, wherein the mammal is further administered a therapeutically effective amount of an ABC transporter inhibitor, whereby the neurodegenerative disease is treated or ameliorated in the mammal.

In certain embodiments, the neurodegenerative disease comprises at least one selected from the group consisting of spinal cord injury, Alzheimer's disease, Parkinson's disease, Huntington's disease, prion disease, amyotrophic lateral sclerosis (ALS), a tauopathy, and chronic traumatic encephalopathy. In other embodiments, the disease comprises ALS.

In certain embodiments, the ABC transporter comprises at least one selected from the group consisting of P-gp and BRCP.

In certain embodiments, the drug comprises at least one selected from the group consisting of ceftriaxone; celecoxib; ciliary neurotrophic factor; cobalamin; coenzyme Q; gabapentin; HGF; IGF-I; minocycline; N-acetylcysteine; NDGA; pentoxifylline; riluzole; thalidomide; topiramate; valproic acid; VEGF; vitamin E; zVAD-fmk; a salt or solvate thereof, and any mixtures thereof.

In certain embodiments, the inhibitor comprises at least one selected from the group consisting of elacridar; tariquidar; zosuquidar; ONT-093; laniquidar; a salt or solvate thereof, and mixtures thereof.

In certain embodiments, the composition is formulated for inhalational, oral, rectal, vaginal, parenteral, topical, transdermal, pulmonary, intranasal, buccal, sublingual, ophthalmic, intrathecal, intravenous and/or intragastrical administration. In other embodiments, the drug is administered to the mammal by at least one route selected from the group consisting of inhalational, oral, rectal, vaginal, parenteral, topical, transdermal, pulmonary, intranasal, buccal, sublingual, ophthalmic, intrathecal, intravenous and intragastrical. In yet other embodiments, at least one selected from the group consisting of the drug and inhibitor is part of a pharmaceutical composition. In yet other embodiments, the pharmaceutical composition comprises an extended-release formulation. In yet other embodiments, the drug and the inhibitor are co-administered to the mammal. In yet other embodiments, the drug and the inhibitor are coformulated.

In certain embodiments, administration to the mammal takes place once the mammal develops any symptom of the neurodegenerative disease. In other embodiments, the mammal that is administered the drug and the inhibitor has a higher spinal cord concentration of the drug than a mammal that is administered the drug only. In yet other embodiments, the mammal that is administered the drug and the inhibitor has a higher compound muscle action potential peak amplitude than a mammal that is administered the drug only. In yet other embodiments, the mammal that is administered the drug and the inhibitor has improved survival as compared to a mammal that is administered the drug only. In yet other embodiments, the mammal that is administered the drug and the inhibitor has delayed disease progression as compared to a mammal that is administered the drug only. In yet other embodiments, the mammal experiences no significant hepatotoxicity when administered the drug and the inhibitor.

In certain embodiments, the mammal is a rodent or a primate. In other embodiments, the primate is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A: Densitometric analysis of P-gp protein expression in lumbar spinal cord showed an increase (1.2- to 1.5-fold, depending on the patient) in sporadic (sALS) and familial (fALS) ALS compared to non-neuromuscular controls and a patient with Friedreich's Ataxia, a different neurological, spinal neuron disease. FIG. 1B: Immunohistochemistry of lumbar spinal cord sections shows the colocalization of P-gp with the endothelial cell marker, von Willebrand Factor. P-gp expression was higher in endothelial cells of ALS patients in the ventral horn of lumbar spinal cord compared to controls (scale bar=20 μm). FIG. 1C: Levels of P-gp expression in the lumbar spinal cord and the hippocampus, an unaffected brain region, of the same ALS patient were compared. P-gp expression increases are tissue specific with higher levels of P-gp expression in the spinal cord of the ALS patient compared to the unaffected area (hippocampus) (scale bar=20 μm). Thus, in ALS patients there was a tissue-specific increase in P-gp protein expression, which was selective to endothelial cells at the level of the BSCB.

FIGS. 2A-2E illustrate the finding that P-gp substrate disposition is altered in SOD1-G93A mice compared to wild-type (WT), and genetic inhibition of P-gp increases the effectiveness of riluzole in SOD1-G93A mice. A specific P-gp substrate, LD800, was injected intraperitoneally into WT, P-gp knockout (P-gp$^{-/-}$), and symptomatic SOD1-G93A mice. Symptomatic SOD1-G93A mice had decreased accumulation of LD800 into the spinal cord compared to WT and P-gp$^{-/-}$ mice (P=0.021 and P<0.001, respectively; FIGS. 2A and 2B). Riluzole is a P-gp substrate and has increased spinal cord (FIG. 2C) and total CNS (FIG. 2D) penetration in P-gp knockout mice. WT and P-gp$^{-/-}$ mice were acutely treated with intraperitoneal injections of riluzole, and the concentrations of riluzole in the plasma and spinal cord tissue were determined via mass spectrometry. FIG. 2C: The percent of riluzole accumulation, normalized to riluzole plasma concentrations, in the spinal cords of P-gp$^{-/-}$ mice was significantly higher than the amount of riluzole in WT mice (20.9±4.3% and 8.4±2.2%, respectively; P=0.028). FIG. 2D: Accumulation of riluzole in the total CNS (brain and spinal cord) was also significantly higher in P-gp$^{-/-}$ compared to WT mice (31.9±4.7% and 15.6±2.0%, respectively; P=0.010). FIG. 2E: As compared to untreated P-gp$^{-/-}$ SOD1-G93A mice and SOD1-G93A riluzole-treated mice, P-gp$^{-/-}$::SOD1-G93A riluzole-treated mice had a trend toward increased survival (165.2±2.89, 162.0±2.51, and 176.0±4.2, respectively; n=5-6).

FIGS. 3A-3E illustrate that chronic elacridar treatment alone does not alter survival or P-gp expression levels, but does increase riluzole accumulation in SOD1-G93A mouse spinal cord. FIG. 3A: Chronic treatment of elacridar, beginning at disease onset, was safe and did not alter disease progression in the SOD1-G93A ALS mice (Log-rank Mantel-Cox, $\chi^2$=0.046, P=0.830). FIG. 3B: P-gp expression levels in riluzole and riluzole+elacridar-treated mice were not altered. FIG. 3C: Penetration of riluzole in the spinal cord of symptomatic 140-day-old mice co-treated with elacridar was measured by mass spectrometry compared to riluzole-only-treated mice. Significantly higher levels of riluzole were detected in riluzole+elacridar-treated mice compared to riluzole+placebo-treated aged-matched 140-day-old ALS mice (295±70.9%; P=0.016). FIG. 3D: Periodic acid Schiff staining of liver sections from riluzole+placebo-treated mice and riluzole+elacridar-treated mice (scale bar=50 m). Chronic treatment with riluzole and elacridar did not cause overt toxicity to the liver of SOD1-G93A mice compared to riluzole treatment alone. FIG. 3E: SOD1-G93A study mice had the same levels of the human transgene as quantified by qRT-PCR of DNA isolated from mouse tail. Mice displaying higher or lower copy numbers were excluded.

FIGS. 4A-4G illustrate that cotreatment with riluzole and elacridar increases survival, NMJ function, behavior, and motor neuron counts compared to riluzole treatment alone. FIG. 4A: Cotreatment of riluzole+elacridar (165±2.1 days) significantly extended survival compared to control+placebo (156.7±2.8 days) and riluzole+placebo (159.7±1.9 days) groups (Log-rank Mantel-Cox, $\chi^2=7.292$, P=0.026; Logrank test for trend, $\chi^2=6.615$, P=0.010; Gehan-Breslow-Wilcoxon, $\chi^2=8.226$, P=0.016). FIGS. 4B-4C: Compound muscle action potentials (CMAPs) had higher peak amplitudes in 140 day riluzole+elacridar-treated mice compared to age-matched riluzole+placebo-treated mice (7.48±0.67 mV and 5.00±0.67 mV, respectively; P=0.017). FIG. 4D: Riluzole+elacridar treatment sustained higher CMAP values throughout treatment compared to riluzole+placebo treatment. FIG. 4E: In the riluzole+elacridar-treated mice, the slope of hind limb strength decline was significantly decreased compared to the riluzole+placebo group (P<0.001). FIGS. 4F-4G: Quantification (neurons larger than 400 μm) and stained lumbar spinal cord tissue sections of motor neurons in the ventral horn of SOD1-G93A mice. Food intake did not differ significantly between the any of the groups.

DETAILED DESCRIPTION OF THE INVENTION

Figure 1A:
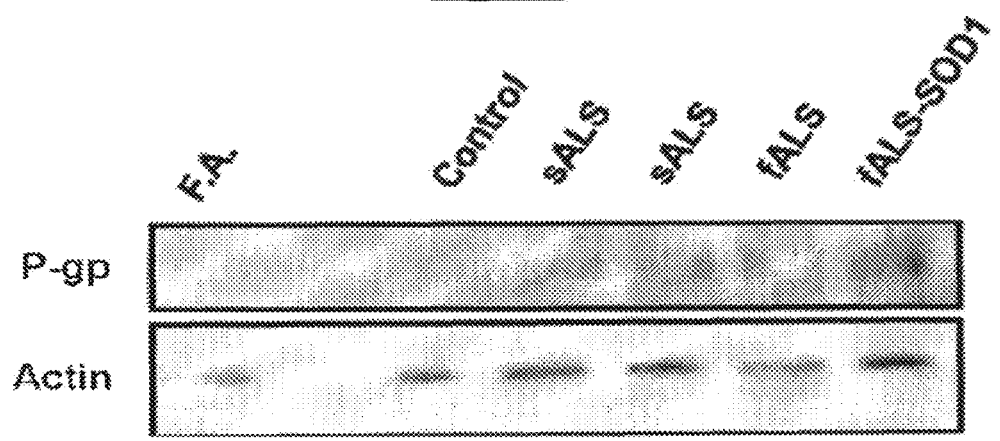
FIGS. 1A-1C illustrate the finding that ALS patients have tissue-specific increases in P-gp protein expression. Protein expression of P-gp in ALS patients compared to controls and levels of P-gp in diseased versus non-diseased tissue areas were examined.

The present invention relates to the unexpected discovery that co-administration of an ABC transporter inhibitor increases the bioavailability and efficacy of a neurodegenerative disease drug in a mammal, wherein the drug is itself a substrate of a ABC transporter. In certain embodiments, the co-administration of the two compounds causes no significant hepatotoxicity in the mammal.

In one aspect, the invention includes a method of treating a neurodegenerative disease in a mammal in need thereof. In certain embodiments, the method comprises administering to the mammal a therapeutically effective amount of a neurodegenerative disease drug, wherein the mammal is further administered at least one ABC transporter inhibitor.

Research has identified several pathogenic mechanisms underlying ALS, but unfortunately clinical trials designed to interfere with these toxic mechanisms have not been successful. One possible explanation for these failures may be the development of pharmacoresistance, which compromises the overall bioavailability of the drugs tested. To this day pharmacoresistance has not been thoroughly studied in the context of ALS.

As reported herein, the inventors have unexpectedly improved the bioavailability and efficacy of an ALS drug by blocking acquired pharmacoresistance. In a non-limiting example, a combination therapy was successfully used in the SOD1-G93A ALS mouse model. Specifically, the combination therapy comprised an ABC transporter inhibitor, elacridar, which blocks P-gp and BCRP (two transporters that are involved in ALS pharmacoresistance), and riluzole, the only FDA-approved drug to treat ALS. By administering elacridar in combination with riluzole in a mammal, riluzole concentrations were increased in the central nervous system, motor performance was enhanced, and the lifespan of ALS mice was increased as compared to untreated mice or mice treated with riluzole only. These studies indicate that riluzole efficacy may be improved by blocking pharmacoresistance in ALS patients.

In one aspect, the present invention is applicable to any ALS drug, currently known or developed anytime in the future, whose activity is decreased because of pharmacoresistance. In another aspect, the present invention is applicable to any neurodegenerative disease drug which activity is decreased because of pharmacoresistance. Restricted drug penetration into the central nervous system is a common challenge in treating neurodegenerative disorders, and combination of the neurodegenerative disease drug with an ABC transporter inhibitor has been discovered herein to improve the bioavailability and efficacy of a drug so restricted. Alterations in ABC transporter expression have been identified, in non-limiting examples, in spinal cord injury, Alzheimer's disease and Parkinson's disease.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and pharmacology are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20%, ±10%, ±5%, +1%, or +0.1% from the specified value, as such variations are appropriate to perform the disclosed methods.

As used herein, the term "ALS" or "Lou Gehrig's disease" may be used interchangeably to refer to amyotrophic lateral sclerosis.

As used herein, the term "BCRP" refers to breast cancer resistance protein.

As used herein, the term "ceftriaxone" refers to (6R,7R)-7-{[(2Z)-2-(2-amino-1,3-thiazol-4-yl)-2-(methoxyimino)acetyl]amino}-3-{[(2-methyl-5,6-dioxo-1,2,5,6-tetrahydro-1,2,4-triazin-3-yl)sulfanyl]methyl}-8-oxo-5-thia-1-azabicyclo[4.2.0]oct-2-ene-2-carboxylic acid, or a salt or solvate thereof.

As used herein, the term "celecoxib" refers to 4-[5-(4-methylphenyl)-3-(trifluoromethyl)pyrazol-1-yl]benzenesulfonamide, or a salt or solvate thereof.

As used herein, the term "CNS" refers to central nervous system.

As used herein, the term "elacridar" refers to N-[4-[2-(3,4-dihydro-6,7-dimethoxy-2(1H)-isoquinolinyl)ethyl]phenyl]-9,10-dihydro-5-methoxy-9-oxo-4-acridine carboxamide, or a salt or solvate thereof.

As used herein, the term "gabapentin" refers to 2-[1-(aminomethyl)cyclohexyl]acetic acid, or a salt or solvate thereof.

As used herein, the term "HGF" refers to hepatocyte growth factor.

As used herein, the term "IGF-I" refers to insulin-like growth factor 1.

"Instructional material," as that term is used herein, includes a publication, a recording, a diagram, or any other medium of expression that may be used to communicate the usefulness of the compounds and/or compositions of the invention. In some instances, the instructional material may be part of a kit useful for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the compounds and/or compositions of the invention or be shipped together with a container that contains the compounds and/or compositions. Alternatively, the instructional material may be shipped separately from the container with the intention that the recipient uses the instructional material and the compound and/or composition cooperatively. For example, the instructional material is for use of a kit; instructions for use of the compound and/or composition; or instructions for use of a formulation of the compound and/or composition.

As used herein, the term "laniquidarmnnethyl" refers to 11-(1-{2-[4-(quinolin-2-yl methoxy)phenyl]ethyl}piperidin-4-ylidene)-6,11-dihydro-5H-imidazo[2,1-b][3]benzazepine-3-carboxylate, or a salt or solvate thereof.

As used herein, the term "minocycline" refers to (2E,4S,4aR,5aS,12aR)-2-(aminohydroxymethylidene)-4,7-bis(dimethylamino)-10,11,12a-trihydroxy-4a,5,5a,6-tetrahydro-4H-tetracene-1,3,12-trione, or a salt or solvate thereof.

As used herein, the term "NDGA" refers to 4,4'-(2,3-dimethylbutane-1,4-diyl) dibenzene-1,2-diol, or a salt or solvate thereof.

As used herein, a "neurodegenerative disease drug" refers to a compound (such as but not limited to a small molecule, nucleic acid, peptide, protein or antibody) that is useful in treating a neurodegenerative disease, a symptom of a neurodegenerative disease or the potential to develop a neurodegenerative disease. In certain embodiments, administration of the neurodegenerative drug has the purpose to cure, heal, alleviate, relieve, alter, remedy, ameliorate, improve or affect the neurodegenerative disease, the symptoms of the neurodegenerative disease, or the potential to develop the neurodegenerative disease.

As used herein, the term "ONT-093" refers to (E)-4,4'-(2-(4-(3-ethoxyprop-1-en-1-yl)phenyl)-1H-imidazole-4,5-diyl)bis(N-isopropylaniline), or a salt or solvate thereof.

As used herein, the term "patient" or "individual" or "subject" refers to a human or a non-human mammal. Non-human mammals include, for example, livestock and pets, such as ovine, bovine, porcine, canine, feline and murine mammals. In certain embodiments, the patient, individual or subject is human.

As used herein, the term "pentoxifylline" refers to 3,7-dimethyl-1-(5-oxohexyl)-3,7-dihydro-1H-purine-2,6-dione, or a salt or solvate thereof.

As used herein, the terms "pharmaceutically effective amount" and "effective amount" and "therapeutically effective amount" refer interchangeably to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "P-gp" or "Pgp" refers to P-glycoprotein.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, f-hydroxybutyric, salicylic, galactaric and galacturonic acid. Suitable pharmaceutically acceptable base addition salts of compounds of the invention include, for example, ammonium and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "pharmaceutical composition" or "composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, inhalational, rectal, vaginal, transdermal, intranasal, buccal, sublingual, parenteral, intrathecal, intragastrical, ophthalmic, pulmonary and topical administration.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "riluzole" refers to 6-(trifluoromethoxy)benzothiazol-2-amine, or a salt or solvate thereof.

As used herein, the term "solvate" refers to a complex with one or more solvent molecules, which may comprise water, methanol, ethanol, 1-propanol, 2-propanol, DMSO, DMF, ethyl ether, acetone, and/or MTBE, and the like.

As used herein, the term "substrate" as relating to a drug efflux transporter refers to a compound (such as a small molecule compound, peptide or protein) that is transported across an extra- or intracellular membrane by the drug efflux transporter.

As used herein, the term "thalidomide" refers to (RS)-2-(2,6-dioxopiperidin-3-yl)-1H-isoindole-1,3(2H)-dione, or a salt or solvate thereof.

As used herein, the term "tariquidar" refers to N-[2-[[4-[2-(6,7-dimethoxy-3,4-dihydro-1H-isoquinolin-2-yl)ethyl]phenyl]carbamoyl]-4,5-dimethoxyphenyl]quinoline-3-carboxamide, or a salt or solvate thereof.

As used herein, the term "topiramate" refers to 2,3:4,5-bis-O-(1-methyl ethylidene)-beta-D-fructopyranose sulfamate, or a salt or solvate thereof.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

As used herein, the term "valproic acid" refers to 2-propylpentanoic acid, or a salt or solvate thereof.

As used herein, the term "VEGF" refers to vascular endothelial growth factor.

As used herein, the term "zVAD-fmk" refers to N-[(phenylmethoxy)carbonyl]-L-valyl-N-[(1S)-3-fluoro-1-(2-methoxy-2-oxoethyl)-2-oxopropyl]-L-alaninamide, or a salt or solvate thereof.

As used herein, the term "zosuquidar" refers to (2R)-1-{4-[(1aR,10bS)-1,1-difluoro-1,1a,6,10b-tetrahydrodibenzo[a,e]cyclopropa[c][7]annulen-6-yl}-3-(quinolin-5-yloxy)propan-2-ol, or a salt or solvate thereof.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

DESCRIPTION

The studies described herein show that a P-gp/BCRP-driven pharmacoresistance limits the bioavailability of ALS therapeutics using riluzole, which is the only FDA-approved drug for ALS and a substrate of P-gp and BCRP. ALS mice (SOD1-G93A) were treated with riluzole and elacridar to block P-gp and BCRP, and monitored for survival as well as behavioral and physiological parameters. Riluzole, which normally is not effective when given to a patient at onset of symptoms, was effective in the ALS mice when administered in combination with the P-gp/BCRP inhibitor elacridar. Chronic elacridar treatment increased riluzole CNS penetration, improved behavioral measures, including muscle function, slowing down disease progression, and significantly extending survival. The results described herein improved riluzole efficacy with treatment beginning at symptom onset.

The impact of P-gp and drug efflux is routinely considered in drug development, but tests are normally performed in healthy animals or individuals to determine whether a drug can cross the blood-brain barrier (BBB). The data presented herein indicates that proper pharmacodynamic and pharmacokinetic studies must be analyzed in patients and disease-relevant models rather than in normal subjects, and that P-gp and BCRP function, in particular, needs to be considered in the context of ALS over disease progression when these two drug efflux transporters begin to effectively pump out therapeutics and when their function increases incrementally with the disease.

Administration of riluzole along with P-gp blockage effectively maintained functional motor neurons, as shown by the CMAPs and behavioral results, and ultimately slowed disease. Thus, the studies show that pharmacologically inhibiting P-gp and BCRP transporter activity can improve ALS pharmacotherapy.

Riluzole is the only moderately effective drug available for ALS treatment and it is also a substrate for P-gp and BCRP. Additionally, riluzole is the only drug which marginal and inconsistent effects in mice translated into a consistent effect in patients. The data presented herein clearly demonstrate that, by blocking P-gp and BCRP, it is possible to enhance riluzole CNS penetration in mice, ultimately restoring its efficacy even when administration begins at onset. Without wishing to be limited by any theory, as the data indicate that riluzole penetration is inversely correlated to riluzole's responsiveness in mice, the decrease in riluzole efficacy observed in patients as disease progresses may derive from the parallel disease-driven increase in pharmacoresistance. As seen in the clinic, there is variability in riluzole efficacy across patients, which may be attributable to individual variations in expression levels of drug efflux transporters. Revisiting riluzole therapy by inhibiting pharmacoresistance may improve quality of life of ALS patients.

Further, targeting P-gp and BCRP has broader implications for ALS therapeutics that go beyond riluzole itself. P-gp and, to a lesser extent, BCRP have broad substrate specificity, and their activities limit bioavailability of multiple drugs. The present data indicate that the same mechanism of acquired pharmacoresistance might apply to other ALS therapeutics, and that blocking P-gp and BCRP with elacridar or similar transporters' inhibitors might also improve delivery, and ultimately, efficacy, of other candidate drugs. In certain embodiments, P-gp and BCRP are the two efflux transporters specifically upregulated in ALS. In other embodiments, P-gp/BCRP inhibition should be considered when designing future pre-clinical and clinical trials with drugs which bioavailability is limited by these two transporters. In yet other embodiments, when designing ALS trials, rather than focusing on increasing the dose of the drug to maximize its effect, P-gp and BCRP are targeted as an effective way to control and improve bioavailability as disease progresses. In yet other embodiments, increasing the ALS drug dose is not be as effective as it might be expected, because disease pathogenic mechanisms continue to incrementally upregulate P-gp and BCRP expression levels and function, effectively pumping the drug out of the CNS regardless of the original dose.

Without wishing to be limited by any theory, increasing ALD drug doses may not be an effective treatment approach. In one aspect, these transporters depend on ATP to extrude their substrates. This characteristic renders them less sensitive to saturation under conditions of ionic unbalances often occurring in disease or in situations of increased substrate concentrations. Regardless of the substrate concentrations (e.g., riluzole), ATP-dependent P-gp and BCRP would still be able to function at no saturation. In another aspect, higher systemic doses of ALS dosing might increase the chances of hepatotoxicity as the ALS-driven increase in P-gp and BCRP seems to be tissue specific, and using elacridar may be the way to just increase riluzole CNS concentrations without overt toxicity.

Overall, the present studies suggest that to maintain efficacious levels of therapeutics throughout disease progression adjusting doses of elacridar (or other more potent and selective P-gp/BCRP inhibitors) may be the most valuable solution. This approach may be used to improve the effects of riluzole in patients as well as reevaluate other drugs that failed in preclinical and clinical trials. In certain embodiments, evaluation of the contribution of P-gp and BCRP altering drug bioavailability and therapeutic efficacy of new ALS therapeutics is performed on a drug-to-drug and patient-to-patient basis.

Compositions

The compounds included in the compositions useful within the invention may be obtained from commercial sources and/or synthesized using techniques well-known in the art of organic synthesis.

The compositions useful within the invention may include a neurodegenerative disease drug or a salt or solvate thereof. In certain embodiments, the neurodegenerative disease comprises ALS. In other embodiments, the drug is a substrate of an ABC transporter inhibitor. In yet other embodiments, the ABC transporter comprises at least one selected from the group consisting of P-gp and BRCP.

In certain embodiments, the neurodegenerative disease comprises at least one selected from the group consisting of spinal cord injury, Alzheimer's disease, Parkinson's disease, Huntington's disease, prion disease, amyotrophic lateral sclerosis, a tauopathy, and chronic traumatic encephalopathy.

In certain embodiments, the neurodegenerative drug comprises at least one selected from the group consisting of: ceftriaxone (also known as (6R,7R)-7-{[(2Z)-2-(2-amino-1,3-thiazol-4-yl)-2-(methoxyimino)acetyl]amino}-3-{[(2-methyl-5,6-dioxo-1,2,5,6-tetrahydro-1,2,4-triazin-3-yl)thio]methyl}-8-oxo-5-thia-1-azabicyclo[4.2.0]oct-2-ene-2-carboxylic acid); celecoxib (also known as 4-[5-(4-methylphenyl)-3-(trifluoromethyl)pyrazol-1-yl]benzenesulfonamide); ciliary neurotrophic factor; cobalamin (including cyano-, hydroxo-, methyl-, and adenosyl-cobalamain); coenzyme Q (also known as 2-[(2E,6E,10E,14E,18E,22E,26E,30E,34E)-3,7,11,15,19,23,27,31,35,39-decamethyltetraconta-2,6,10,14,18,22,26,30,34,38-decaenyl]-5,6-dimethoxy-3-methylcyclohexa-2,5-diene-1,4-dione); gabapentin (also known as 2-[1-(aminomethyl)cyclohexyl]acetic acid); HGF (hepatocyte growth factor); IGF-I (insulin-like growth factor 1); minocycline (also known as (2E,4S,4aR,5aS,12aR)-2-(amino-hydroxy-methylidene)-4,7-bis(dimethylamino)-10,11,12a-trihydroxy-4a,5,5a,6-tetrahydro-4H-tetracene-1,3,12-trione); N-acetylcysteine; NDGA (also known as nordihydroguaiaretic acid, or 4,4'-(2,3-dimethylbutane-1,4-diyl)dibenzene-1,2-diol); pentoxifylline (also known as 3,7-dimethyl-1-(5-oxohexyl)-3,7-dihydro-1H-purine-2,6-dione); riluzole (also known as 6-(trifluoromethoxy) benzothiazol-2-amine); thalidomide (also known as (RS)-2-(2,6-dioxopiperidin-3-yl)-1H-isoindole-1,3(2H)-dione); topiramate (also known as 2,3:4,5-bis-O-(1-methylethylidene)-beta-D-fructopyranose sulfamate); valproic acid (also known as 2-propylpentanoic acid); VEGF (vascular endothelial growth factor); vitamin E; zVAD-fmk (also known as benzyloxycarbonyl-Val-Ala-Asp (OMe)-fluoromethylketone); a salt or solvate thereof, and mixtures thereof.

The compositions useful within the invention may include an ABC transporter inhibitor. In certain embodiments, the ABC transporter comprises at least one selected from the group consisting of P-gp and BRCP.

In certain embodiments, the ABC transporter inhibitor includes at least one selected from the group consisting of: elacridar (also known as N-[4-[2-(6,7-dimethoxy-3,4-dihydro-1H-isoquinolin-2-yl)ethyl]phenyl]-5-methoxy-9-oxo-10H-acridine-4-carboxamide); tariquidar (also known as N-[2-[[4-[2-(6,7-dimethoxy-3,4-dihydro-1H-isoquinolin-2-yl)ethyl]phenyl]carbamoyl]-4,5-dimethoxyphenyl]quinoline-3-carboxamide); zosuquidar (also known as (2R)-1-{4-[(1aR,10bS)-1,1-difluoro-1,1a,6,10b-tetrahydrodibenzo[a,e]cyclopropa[c][7]annulen-6-yl}-3-(quinolin-5-yloxy) propan-2-ol); ONT-093 (also known as (E)-4,4'-(2-(4-(3-ethoxyprop-1-en-1-yl)phenyl)-1H-imidazole-4,5-diyl)bis (N-isopropylaniline)); laniquidar (also known as methyl 11-(1-{2-[4-(quinolin-2-ylmethoxy)phenyl]ethyl}piperidin-4-ylidene)-6,11-dihydro-5H-imidazo[2,1-b][3]benzazepine-3-carboxylate); a salt or solvate thereof, and any mixtures thereof.

The compositions useful within the invention may include a pharmaceutically acceptable carrier. In certain embodiments, the neurodegenerative drug and the ABC transporter inhibitor are co-formulated.

Methods

The invention includes a method of treating a neurodegenerative disease in a mammal in need thereof. The method comprises administering to the mammal a therapeutically effective amount of a neurodegenerative disease drug, wherein the drug is a substrate of an ABC transporter. According to the method, the mammal is further administered a therapeutically effective amount of an ABC transporter inhibitor, whereby the neurodegenerative disease is treated in the mammal.

In certain embodiments, the neurodegenerative disease comprises at least one selected from the group consisting of spinal cord injury, Alzheimer's disease, Parkinson's disease, Huntington's disease, prion disease, ALS, a tauopathy, and chronic traumatic encephalopathy. In other embodiments, the neurodegenerative disease comprises ALS. In yet other embodiments, the ABC transporter comprises at least one selected from the group consisting of P-gp and BRCP.

In certain embodiments, the drug comprises at least one selected from the group consisting of ceftriaxone; celecoxib; ciliary neurotrophic factor; cobalamin; coenzyme Q; gabapentin; HGF; IGF-I; minocycline; N-acetylcysteine; NDGA; pentoxifylline; riluzole; thalidomide; topiramate; valproic acid; VEGF; vitamin E; zVAD-fmk; a salt or solvate thereof, and mixtures thereof. In other embodiments, the ABC transporter inhibitor comprises at least one selected from the group consisting of elacridar; tariquidar; zosuquidar; ONT-093; laniquidar; a salt or solvate thereof, and mixtures thereof.

In certain embodiments, the drug is part of a pharmaceutical composition. In other embodiments, the inhibitor is part of a pharmaceutical composition. In other embodiments, the pharmaceutical composition comprises an extended-release formulation.

In certain embodiments, the drug is administered to the mammal before the inhibitor. In other embodiments, the inhibitor is administered to the mammal before the drug. In yet other embodiments, the inhibitor and the drug are administered to the mammal at about the same time. In yet other embodiments, the drug and the inhibitor are co-administered to the mammal. In yet other embodiments, the drug and the inhibitor are coformulated. In yet other embodiments, the drug and/or the inhibitor is/are administered at or after the onset of any symptom of the disease.

In certain embodiments, the mammal that is administered the drug and the inhibitor has a higher spinal cord concentration of the drug than a mammal that is administered the drug only. In certain embodiments, the mammal that is administered the drug and the inhibitor has a higher compound muscle action potential peak amplitude than a mammal that is administered the drug only. In certain embodiments, the mammal that is administered the drug and the inhibitor has improved survival as compared to a mammal that is administered the drug only. In certain embodiments, the mammal that is administered the drug and the inhibitor has delayed disease progression as compared to a mammal that is administered the drug only.

In certain embodiments, the mammal is a rodent or a primate. In other embodiments, the primate is a human. In yet other embodiments, the drug is administered to the mammal by at least one route selected from the group consisting of inhalational, oral, rectal, vaginal, parenteral, topical, transdermal, pulmonary, intranasal, buccal, sublingual, ophthalmic, intrathecal, intravenous and intragastrical.

Combination Therapies

The compositions useful within the present invention are intended to be useful in the methods of present invention in combination with one or more additional compounds useful for treating the diseases or disorders contemplated within the invention. These additional compounds may comprise compounds of the present invention or compounds, e.g., commercially available compounds, known to treat, prevent, or reduce the symptoms of the diseases or disorders contemplated within the invention.

A synergistic effect may be calculated, for example, using suitable methods such as, for example, the Sigmoid-$E_{max}$ equation (Holford & Scheiner, 1981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to, around the time, or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions useful within the present invention to a patient, such as a mammal, such as a human, may be carried out using known procedures, at dosages and for periods of time effective to treat a disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder in the patient. Dosage regimens may be adjusted to provide the optimum therapeutic response. For example, several divided doses may be administered daily or the dose may be proportionally reduced as indicated by the exigencies of the therapeutic situation. In certain embodiments, an effective dose range for a therapeutic compound of the invention ranges from about 1 to about 5,000 mg/kg of body weight/day. In other embodiments, an effective dose range for a therapeutic compound of the invention ranges from about 100 to about 1,000 mg/kg of body weight/day. In yet other embodiments, an effective dose range for a therapeutic compound of the invention ranges from about 10 to about 50 mg/kg of body weight/day. In yet other embodiments, an effective dose range for a therapeutic compound of the invention ranges from about 1 to about 50 mg/kg of body weight/day. In yet other embodiments, an effective dose range for a therapeutic compound of the invention ranges from about 1 to about 10 mg/kg of body weight/day. In yet other embodiments, an effective dose range for a therapeutic compound of the invention is about 2.5 mg/kg of body weight/day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions useful within the invention are formulated using one or more pharmaceutically acceptable excipients or carriers. In certain embodiments, the pharmaceutical compositions of the invention comprise a therapeutically effective amount of a compound useful within the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it may include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions useful within the invention are administered to the patient in dosages that range from one to five times per day or more. In other embodiments, the compositions useful within the invention are administered to the patient in range of dosages that include, but are not limited to, once every day, every two, days, every three days to once a week, and once every two weeks. It will be readily apparent to one skilled in the art that the frequency of administration of the various combination compositions useful within the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In certain embodiments, the dose of a compound is from about 1 mg and about 2,500 mg. In other embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in other embodiments, a dose of a second compound (i.e., a drug used for treating a disease or disorder) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other cognition improving agents.

The term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY—P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease or disorder. Using a wax/pH-sensitive polymer mix, a gastric insoluble composition may be obtained in which the active ingredient is entrapped, ensuring its delayed release.

Parenteral Administration

For parenteral administration, the compounds may be formulated for injection or infusion, for example, intravenous, intramuscular or subcutaneous injection or infusion, or for administration in a bolus dose and/or continuous infusion. Solutions, suspensions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 2003/0147952, 2003/0104062, 2003/0104053, 2003/0044466, 2003/0039688, and 2002/0051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound will depend on the age, sex and weight of the patient, the current medical condition of the patient and the progression of the disease or disorder in the patient being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods:

Animals:

Mice were housed in accordance with Thomas Jefferson University Institutional Animal Care and Use Committee (IACUC) and the NIH Guide for the Care and Use of Laboratory Animals. Mutant SOD1-G93A mice modeling ALS [B6.Cg-Tg(SOD1-G93A)1Gur/J] were purchased from Jackson Laboratories (Sacramento, Calif., catalog no. 004435). Male SOD1-G93A mice were bred with C57BL/6 females. Offspring were genotyped to determine presence of the human SOD1 transgene. As transgene copy number is known to fluctuate and decrease through subsequent breeding generations, quantitative RT-PCR was performed to exclude mice with decreased SOD1 human transgene copy number.

P-glycoprotein knockout mice (P-gp$^{-/-}$) on the FVB/N background were purchased from Taconic (Germantown, N.Y., catalog no. #1487). Prior to crossing with SOD1-G93A mice, P-gp$^{-/-}$ mice were backcrossed to C57BL/6 mice (N=5). After the fifth generation and a homogeneous B6SJL background, P-gp$^{-/-}$ mice were crossed with SOD1-G93A mice and genotyped to determine presence of the SOD1-G93A human transgene. Mice were controlled for human transgene copy number via qRT-PCR.

Drug Treatment and Survival Analysis:

Transgenic mutant SOD1-G93A male mice were used in a preclinical drug study format. Mice were enrolled into one of three treatment groups: control+placebo/elacridar (n=25), riluzole+placebo (n=25), or riluzole+elacridar (n=25).

Riluzole was administered via the chow (125 mg/kg of chow). Elacridar was administered via a time-controlled release pellet (50 mg/10 day release, Innovative Research of America, Sarasota, Fla.), which was implanted subcutaneously in the back of the neck. Control chow was prepared in the same manner as the riluzole chow. To control for the effects of surgical pellet implantation, control and riluzole-treated mice also received placebo pellets every 10 days.

Treatment of riluzole and elacridar began at 100 days of age and continued for the lifespan of all mice. Baseline and study measures were recorded for weight, grip strength, food consumption, and survival. Determination of end-stage was the inability for a mouse to right itself after 30 seconds of being placed on its side.

Grip Strength and Weight Assessment:

Hindlimb grip strength was recorded 2-3 times per week for each mouse. The rate of grip strength deterioration for riluzole+placebo and riluzole+elacridar groups was determined based on the average grip strength per day per mouse and fit to a linear curve. The weights for each mouse was recorded 2-3 times per week for each mouse and the rate of decline was quantified for riluzole+placebo and riluzole+elacridar groups.

Compound Muscle Action Potential (CMAP) Recordings:

Mice were anesthetized with 1% isoflurane and 0.5% oxygen. Following dermatomoty, stainless steel-stimulating needle electrodes were inserted at the sciatic notch, near the sciatic nerve. A ground electrode was placed subcutaneously in the back, and a reference electrode placed subcutaneously at the ankle. The sciatic nerve was stimulated (0.2 ms duration; 1.6 mV amplitude) and the response recorded via a needle electrode inserted into the plantar muscle in the medial half of the foot, following the line connecting the first and fifth tarsal/metatarsal joints. Data was collected using ADI Powerlab 8/30 stimulator and BioAMP amplifier (ADInstruments, Colorado Springs, Colo.) and analyzed using Scope 3.5.6 (ADInstruments). The compound muscle action potential (M-wave) amplitude was measured from baseline to peak. Data was averaged between left and right hind limb traces.

In Vivo LD800 Imaging:

LD800 (1 mg/kg) was injected i.p. Twenty minutes later animals were anesthetized with a ketamine:xylazine mixture and sacrificed via cardiac perfusion with heparinized PBS. Spinal cord samples were collected and embedded in low-melting point agarose and sectioned in 750 m thick sections using a tissue chopper (McIlwain Tissue Chopper, The Mickle Laboratory Engineering Company). Spinal cord tissue sections were then imaged with an Odyssey infrared imager (LI-COR Biosciences).

Mass Spectrometry:

Age-matched, adult mice (150 days of age) were injected intraperitoneally with Riluzole.HCl (12 mg/kg). After 1 h, mice were sacrificed with carbon dioxide, blood was collected via cardiac puncture, and mice were flushed with saline (0.9%). Blood was placed in EDTA-coated eppendorf tubes and centrifuged to collect plasma. Brains and spinal cords were harvested and flash frozen. All samples were stored at −80° C. until extraction. For plasma samples, nine volumes ice-cold, 100% ethanol were added to each sample, incubated overnight at 4° C. and centrifuged for 25 min (3,500 rpm, 4° C.). Ethanol supernatant was removed and pellets were dried in a speed vacuum. Pellets were stored at −80° C. Pellets were resuspended in 0.1% formic acid, water bath sonicated for 20 min, and centrifuged at 15 rcf for 30 min. Supernatant was further diluted in 0.1% formic acid, and analyzed by LC-MS/MS on a Thermo LTQ-Orbitrap XL mass spectrometer at the Wistar Proteomics Facility. Riluzole had elution peaks at 17 min, peak areas were used at 5 ppm Mass Accuracy to find relative concentration amounts from standard curve.

Motor Neuron Counts:

Mice were perfused with Dulbecco's phosphate-buffered saline (DPBS) and spinal cord lumbar segments were embedded in OCT freezing medium and stored at −20° C. until sectioned. Forty micrometer fresh frozen tissue sections were dissected using a temperature controlled cryostat (MICROM HM 505 E). Tissue sections were coded blind and processed simultaneously. Sections were fixed with 2.5% paraformaldehyde for 10 min at room temperature. Every second section was stained about 3-4 min with 0.1% cresyl violet acetate and dipped in 95% Ethanol and 95% ethanol+glacial acetic acid to facilitate the staining. Finally, slides were mounted with permount and dried overnight at room temperature. Stained sections were visualized under a 60× oil immersion objective of a bright-field microscope (Olympus). Four sections per animal were analyzed per group (n=7). Large pyramidal motor neurons positively stained for cresyl violet with a prominent nucleus and size at least >20 µm$^2$ were counted. Motor neurons were quantified using the optical fractionator workflow module of stereo investigator software (version 8) employing a grid size 75×75 μm and sampling grid size 100×100 μm. All analysis was carried out by an investigator blinded to the samples. Motor neuron counts per group were later quantified using Student's t-test and represented as average±SEM.

Periodic Acid Schiff Staining:

Saline perfused liver was postfixed with 4% paraformaldehyde for 24 h followed by 24 h incubation in 30% sucrose solution, embedded in OCT solution, and stored at −80° C. until sectioned (10 μm thickness). Sections were hydrated with water, immersed in PAS solutions (Sigma; 395) for 5 min at room temperature, and washed in water. Sections were immersed for 4 min in Schiff's reagent and washed in water for 5 min. Sections were counterstained with hematoxylin solution, dehydrated in ethanol and HemoD solution, mounted, and imaged.

Immunofluorescence of Patient Tissue:

OCT-embedded spinal cord and hippocampus tissue were cryostat sectioned at 10 μm. Slides were rinsed once in 1.5×TBS buffer and postfixed in 4% paraformaldehyde for 10 min at room temperature followed by treatment with antigen unmasking solution for 2 min at −20° C. (33% acetic acid and 66% ethanol). After washing and blocking (2% BSA, 0.3% triton-X, 5% horse serum in 1.5×TBS), slides were incubated with primary antibodies (C219 from Covance 1:50 and vWF from Dako 1:50). After washing, tissue was then incubated with fluorescent secondary antibodies, mounted with DAPI antifade solution, and imaged.

Example

Figure 1B:
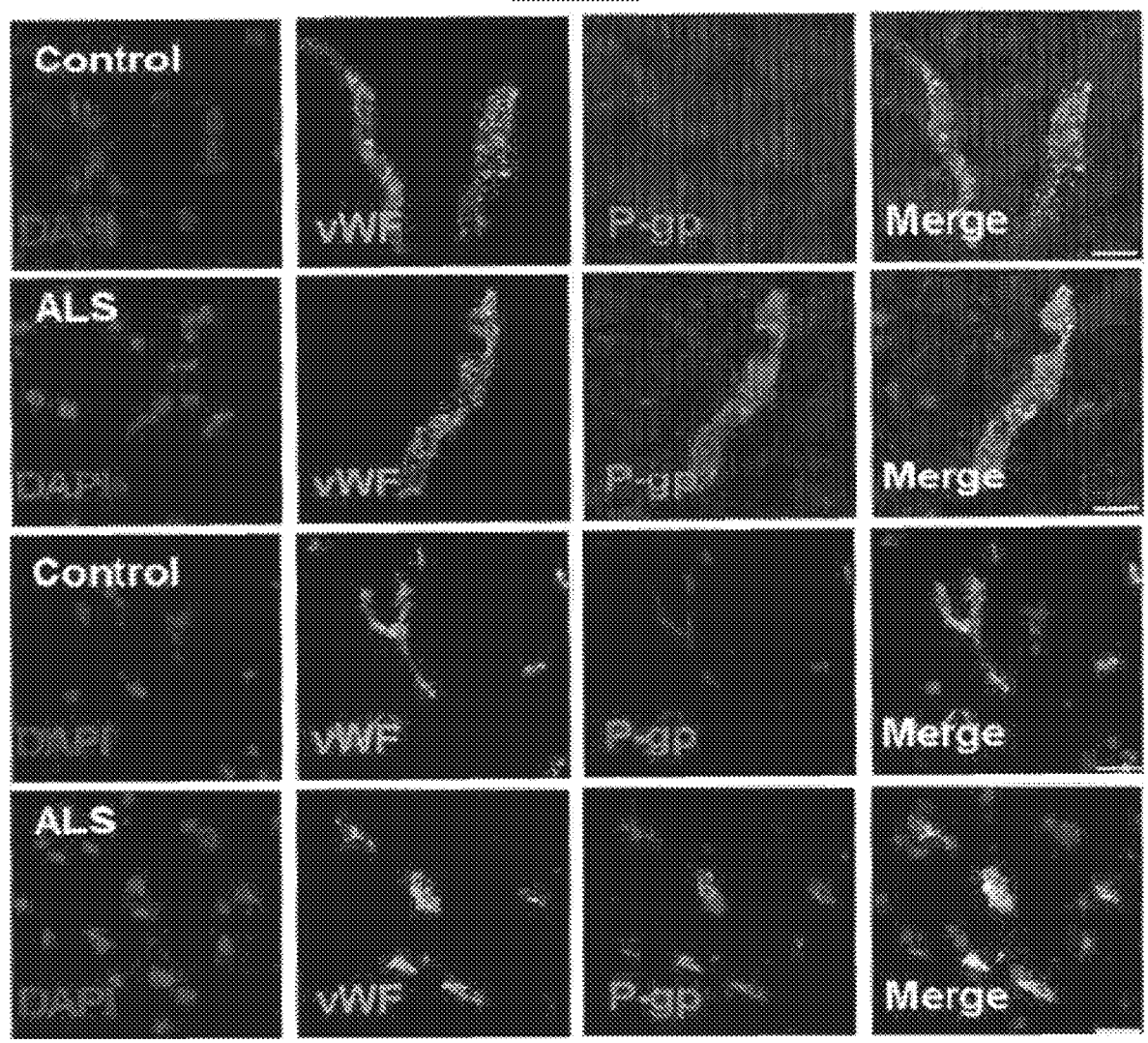
Figure 1C:
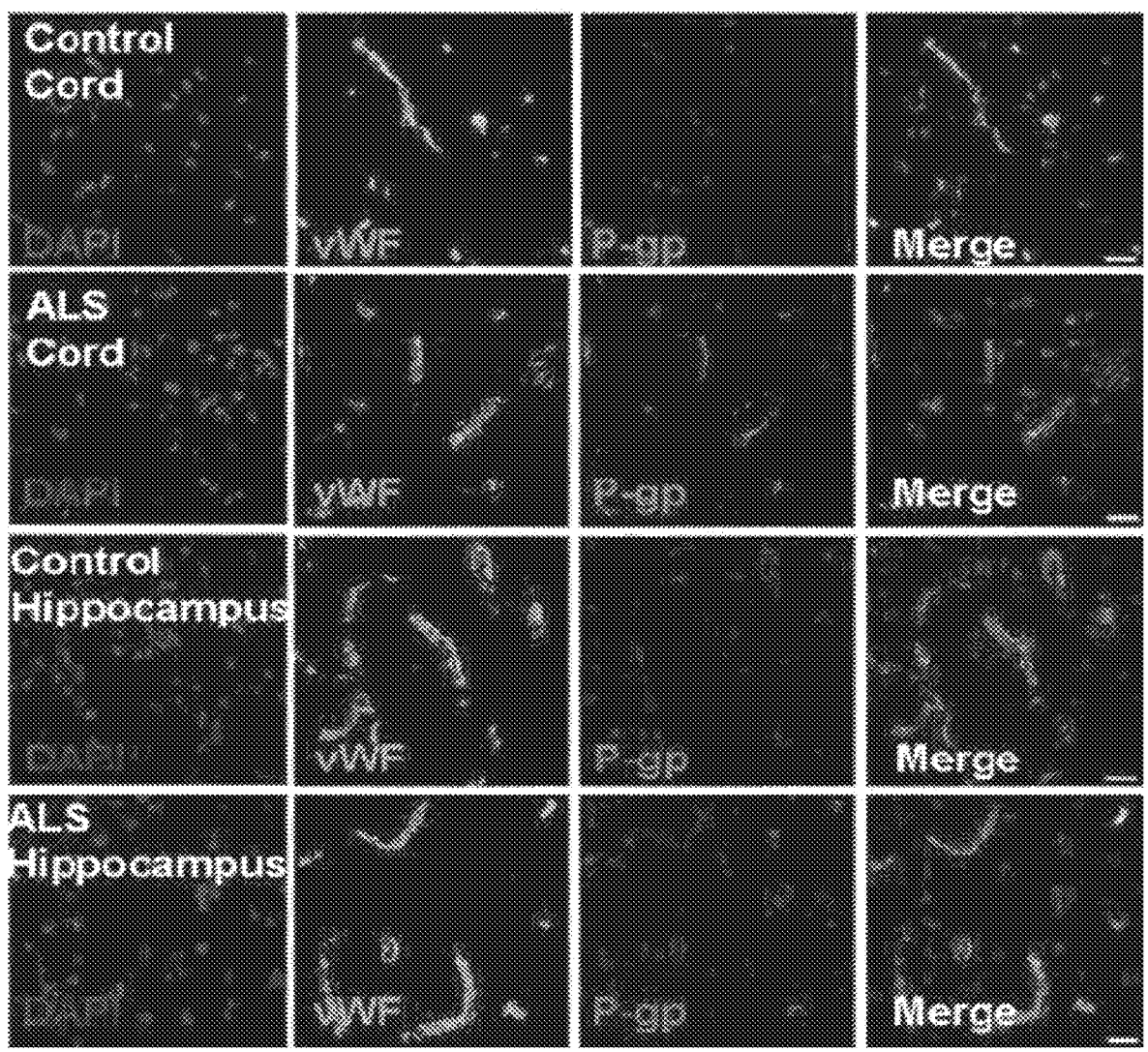

Homogenates of lumbar spinal cords of two sporadic and two familial ALS patients displayed increased levels of P-gp compared to controls, including a control patient with Friedreich's Ataxia (FIG. 1A). By immunohistochemistry, increases in P-gp expression were found in endothelial cells of the BSCB (FIGS. 1B-C). A selective, tissue-specific increase of P-gp expression was found in areas affected by the disease, specifically spinal cord, while P-gp levels remained low in the unaffected hippocampus (FIG. 1C). Microvascular leakage and reduced tight junction protein expression are known to occur in ALS and could contribute to motor neuron damage. Without wishing to be limited by any theory, upregulation of P-gp may occur as a compensatory response to a leaking BSCB.

Figure 2A:
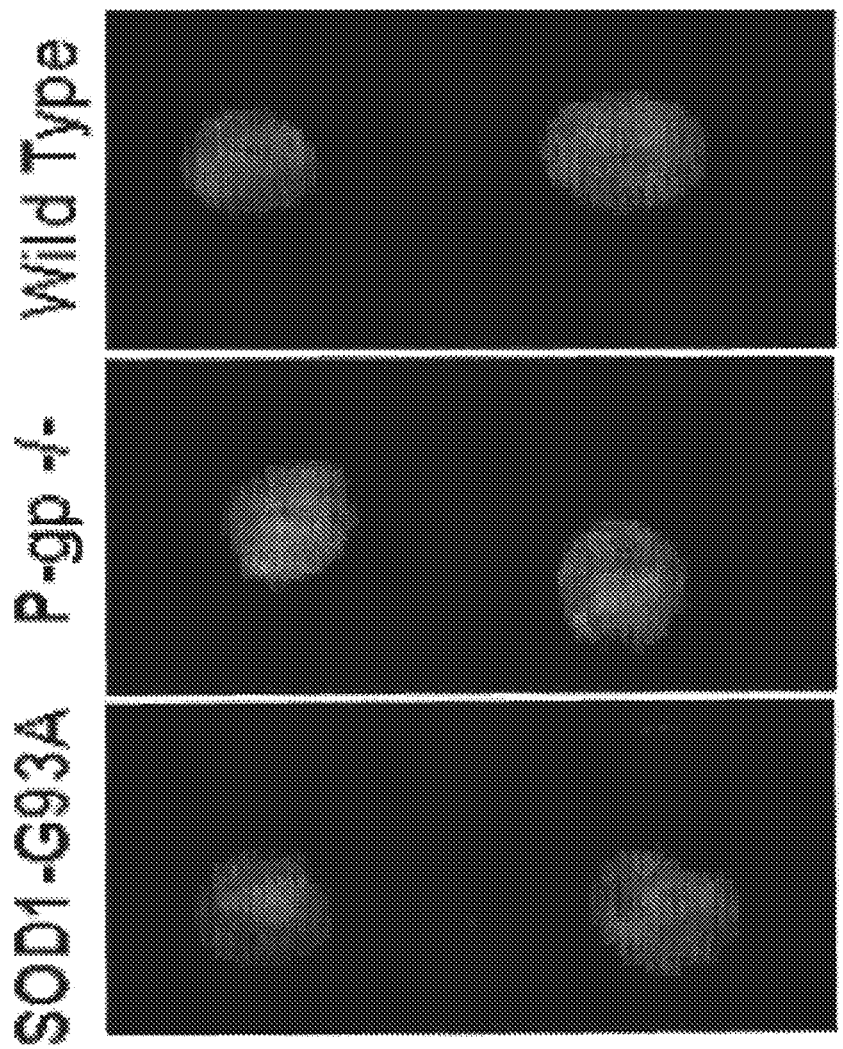
Figure 2B:
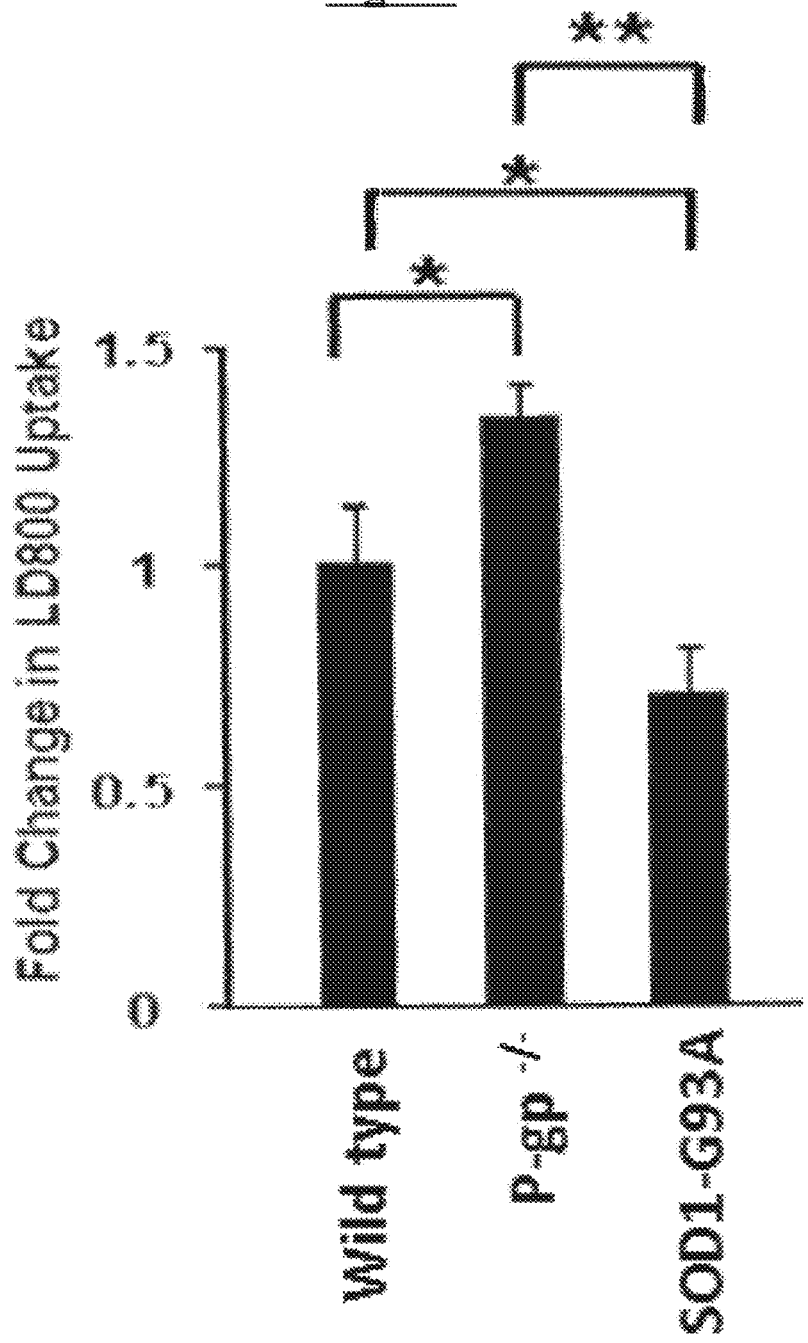

In certain embodiments, activation of P-gp can prevent effective drug delivery in the CNS, reducing drug bioavailability. To demonstrate this, the in vivo accumulation of a specific P-gp substrate, LD800, was examined in the spinal cord of the ALS mouse model where expression and function of P-gp increases as disease progresses. Symptomatic mice had a marked decrease in LD800 accumulation as compared to nontransgenic and P-gp$^{-/-}$ mice (FIGS. 2A-2B).

Figure 2E:
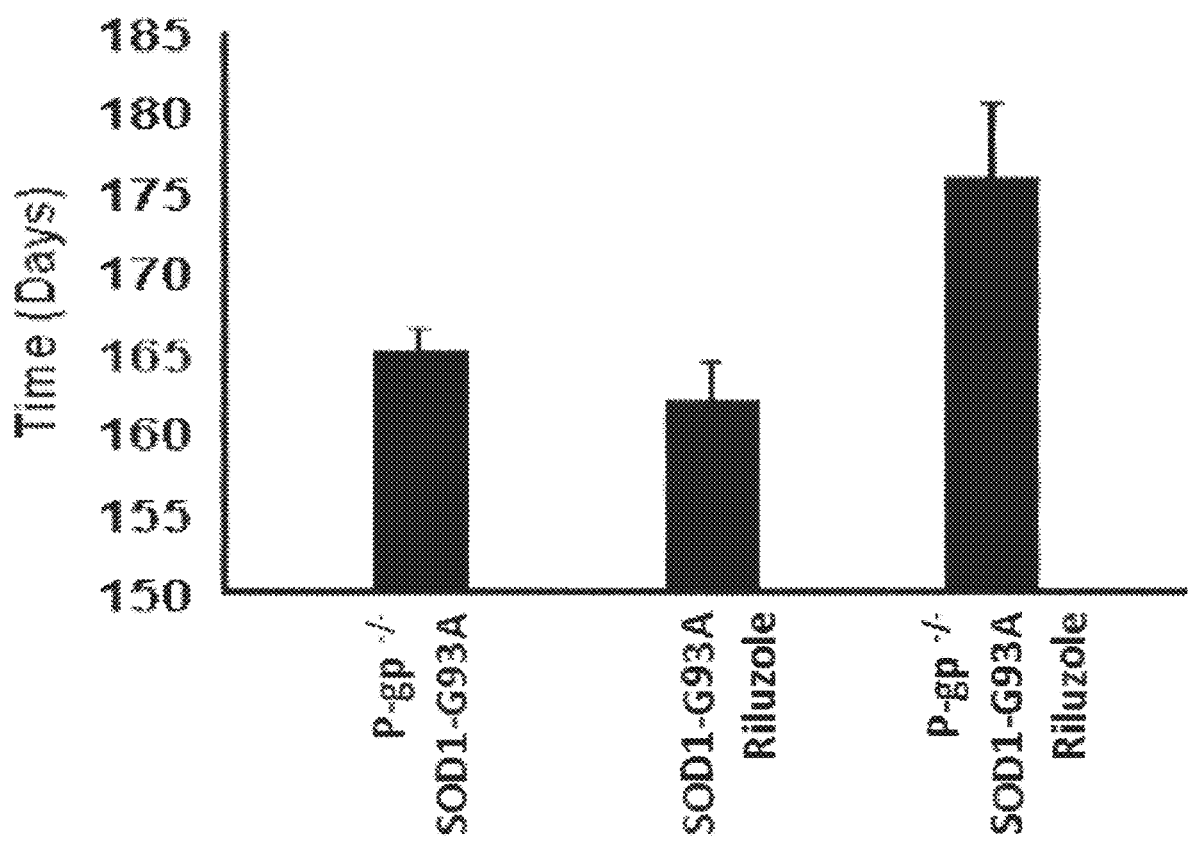

The extent to which P-gp alters riluzole disposition into the CNS was analyzed. The percent of riluzole accumulation in the spinal cord and brain was higher in P-gp$^{-/-}$ mice compared to age-matched, non-transgenic mice (FIGS. 2C-2D). Then, P-gp$^{-/-}$ and SOD1-G93A mice were crossed to obtain ALS mice lacking P-gp (P-gp$^{-/-}$::SOD1-G93A$^{+/-}$). These mice were treated with riluzole beginning at symptom onset (at ~100 days of age). As very low numbers of P-gp$^{-/-}$::SOD1-G93A mice were obtained from these crosses, the analysis was limited to 5-6 mice per group to allow initial evaluation of the impact of P-gp knock down on disease and riluzole penetration. Knocking out P-gp from the ALS mice improved significantly the therapeutic effect of riluzole (FIG. 2E), further strengthening the assumption that as ALS progresses in mice and P-gp and BCRP increase, riluzole penetration and efficacy decrease.

Figure 3A:
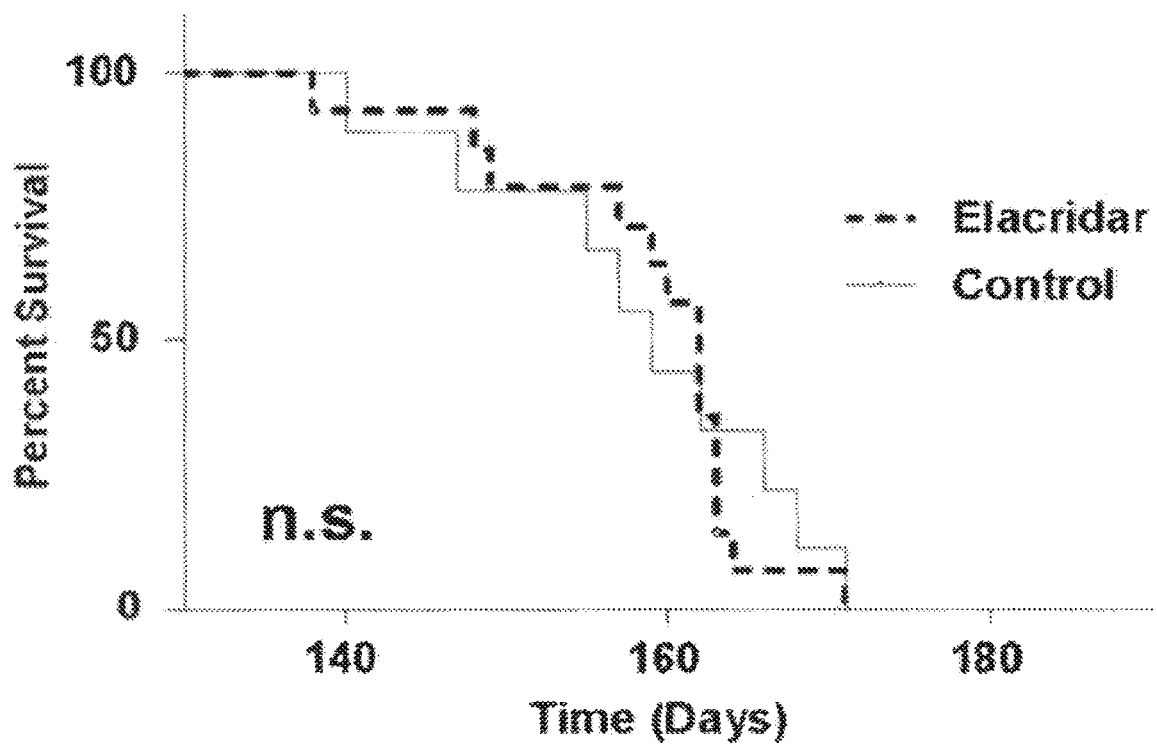
Figure 3B:
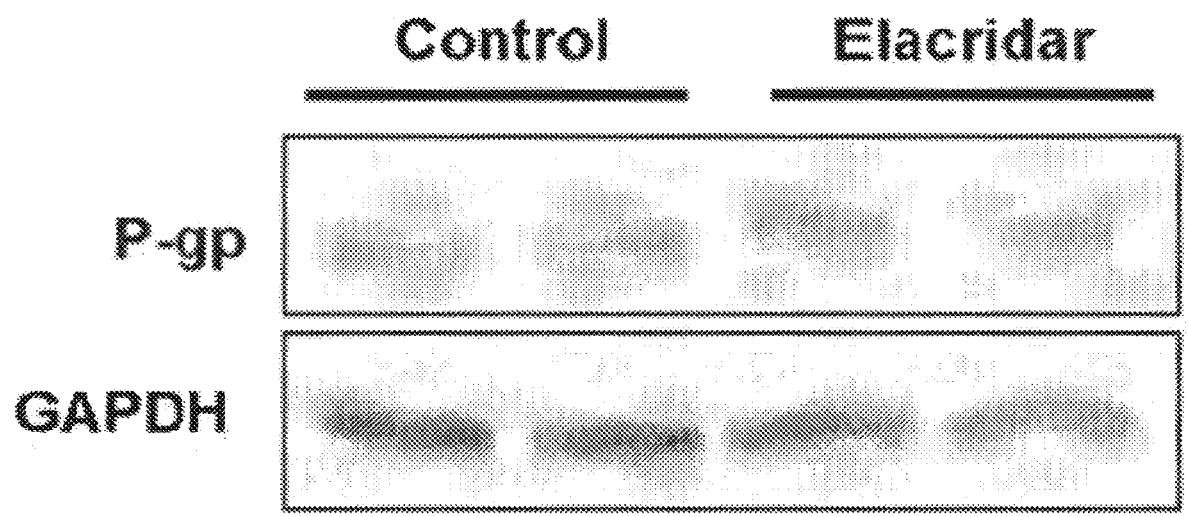
Figure 3C:
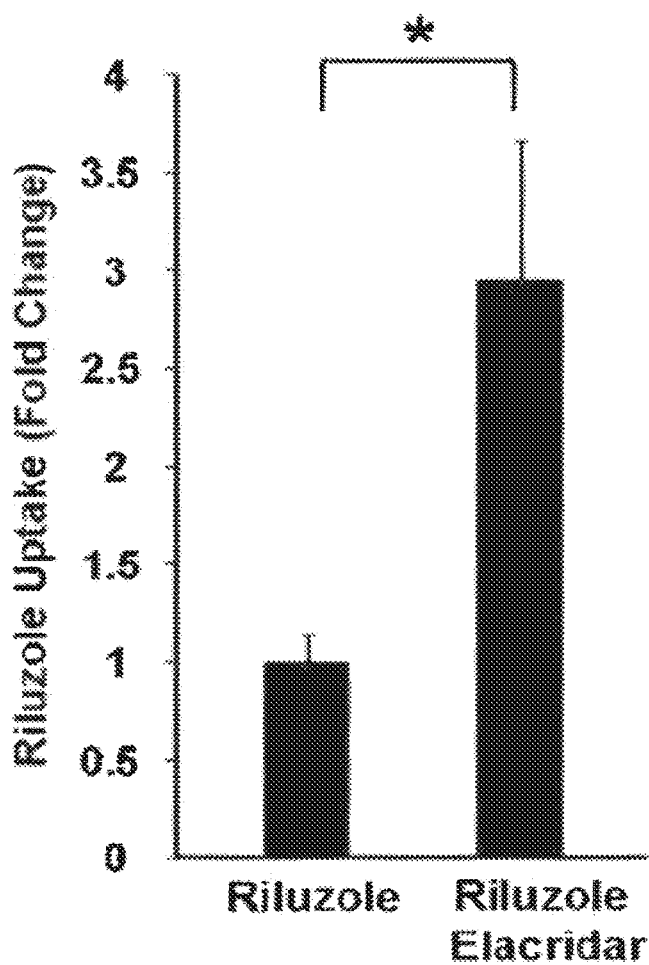
Figure 3D:
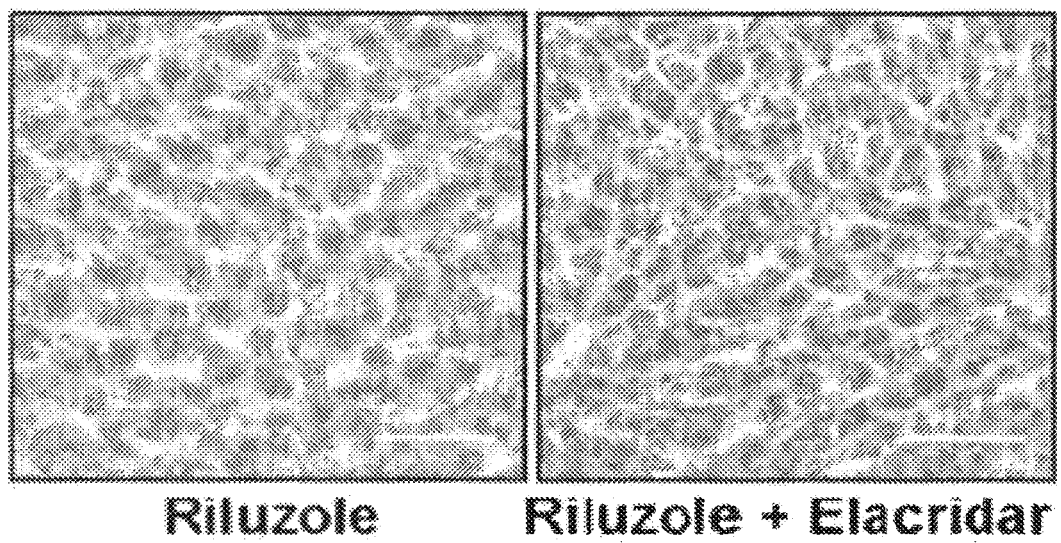

To compensate for this progressive decrease in therapeutic levels of riluzole in the spinal cord of diseased mice, the activity of P-gp and BCRP was pharmacologically inhibited. Inhibitors of drug efflux transporters can be used to restore drug sensitivity in diseases in which the issue of pharmacoresistance is well characterized, such as leukemia, other forms of cancer, and epilepsy. Third-generation inhibitors, such as elacridar (GF120918), are highly specific and tolerated in patients. The mice were treated with elacridar, which provides dual inhibition of P-gp and BCRP. Chronic elacridar treatment, beginning at disease onset, was safe and did not alter disease progression in SOD1-G93A mice (FIG. 3A). As expected, chronic treatment of elacridar did not affect overall expression of P-gp (FIG. 3B) or BCRP; it did inhibit their function, though, resulting in a significant increase in riluzole spinal cord concentrations in diseased mice (FIG. 3C). Despite higher levels of systemic riluzole, the riluzole+elacridar-treated mice did not show signs of liver pathology (FIG. 3D), indicating that elacridar did not cause liver toxicity and that increasing systemic riluzole concentrations via elacridar were not hepatotoxic.

To determine whether the increased drug bioavailability translated into improved efficacy, riluzole was tested as the candidate drug. This drug has a marginal, albeit variable, effect in the SOD1-G93A mice. The riluzole and elacridar treatment was initiated in the mouse models. Most published preclinical studies in mice began riluzole treatment presymptomatically (between 50 and 60 days) and prior to disease onset. This is based on the assumption that high levels of mutant SOD1 expression in mice lead to an "enhanced" disease that needs to be managed aggressively. But most of the compounds tested presymptomatically have only delayed disease onset rather than slowed disease progression with an overall extension of lifespan <10%. Without wishing to be limited by any theory, a delay in onset with pharmacological treatment is not likely to be predictive of how well a drug may perform clinically.

The prior observations showed that P-gp and BCRP function increased beginning at symptom onset and peaked at symptomatic stage, so the riluzole and elacridar treatment was initiated at onset (P100). In addition, without wishing to be limited by any theory, the study can mimic, to the extent possible, the therapeutic regimen of the patients who are treated with riluzole after they are diagnosed with the disease.

Figure 4D:
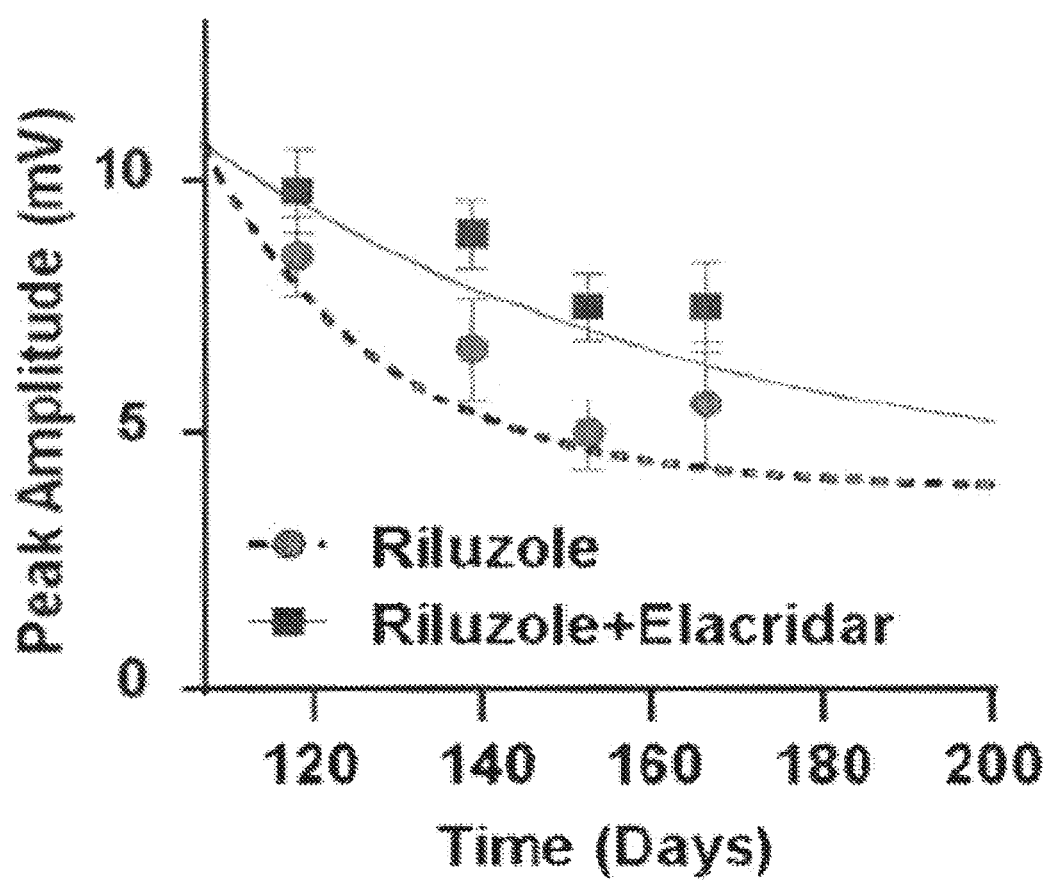

The analysis of the SOD1-G93A mice consisted of three groups of mice (n=25 males/group): (1) control, placebo-treated; (2) riluzole+placebo-treated; and (3) riluzole+elacridar-treated. Copy number of the SOD1-G93A human transgene was controlled (FIG. 3E). Cotreatment using riluzole+elacridar beginning at symptoms onset significantly extended survival compared to control/placebo and riluzole/placebo groups (FIG. 4A). Riluzole alone was not beneficial and did not extend survival compared to control mice. However, when given in combination with elacridar, it significantly slowed disease progression, extending mouse survival by 13% from onset of symptoms (FIG. 4A). This specific effect on disease progression was superior to many pharmacological interventions in ALS mice, which primarily affected disease onset but not duration.

Consecutive surgeries of pellet implantation had negative effects on the mice. The life-span of placebo pellet-implanted SOD1-G93A mice decreased by ~6 days compared to nonsurgery ALS mice (156.7±2.8 days and 162.9±0.69 days, respectively; −3.8%; P<0.05), likely due to the negative impact of multiple pellet implantation surgeries. In certain embodiments, the full potential of the beneficial effect of riluzole+elacridar might have been negatively skewed by the pellet implantation regimen.

Figure 4G:
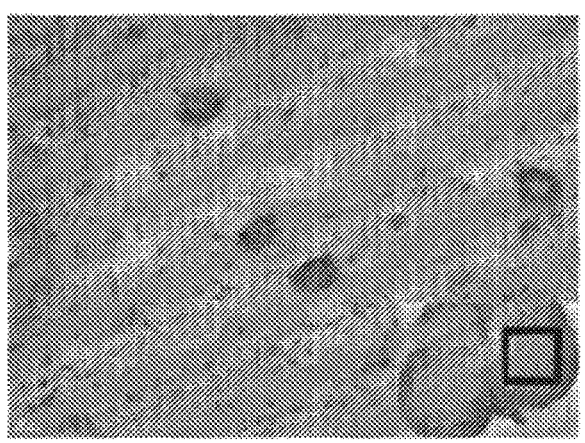
Figure 4G:
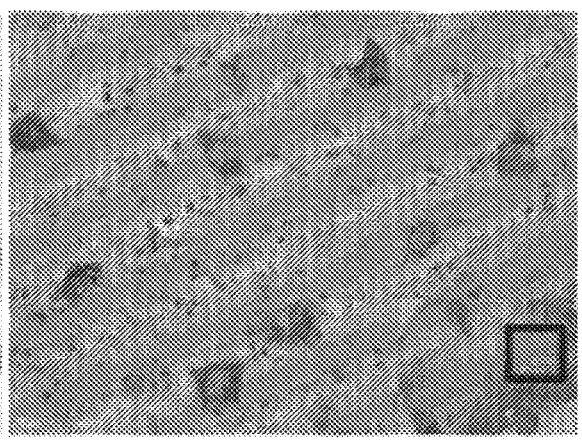

Treatment of riluzole and elacridar significantly improved vital parameters (FIG. 4). Two additional cohorts of mice were treated with riluzole+placebo (n=10) or riluzole+elacridar (n=1), from 100 to 140 days, and electrophysiological recordings from the plantar muscle following sciatic nerve stimulation were performed to measure functional innervation by motor neurons of the lumbar spinal cord (FIGS. 4B-4C). CMAPs had higher peak amplitudes in 140 day riluzole/elacridar mice compared to age-matched riluzole/placebo mice (FIGS. 4B-4C). Throughout the 40-day treatment, the riluzole/elacridar mice maintained significantly higher CMAP values compared to the riluzole/placebo mice (FIG. 4C). In the same mice, hindlimb grip strength was improved (FIG. 4E). There was a trend for an increased number of remaining motor neurons in the lumbar spinal cord of P140 mice cotreated with riluzole and elacridar. In certain embodiments, stopping motor neuron death may not be sufficient to slow disease. In other embodiments, maintaining motor neuron function may be sufficient to slow disease. In yet other embodiments, there is a dissociation between motor neuron death and disease progression in mutant SOD1 mice.

In a non-limiting aspect, accounting for the contribution of ABC transporters to ALS pharmacoresistance may both improve the modest effects of riluzole therapy and allow for a reevaluation of previously discarded ALS drugs.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or ameliorating a neurodegenerative disease in a mammal in need thereof, the method comprising administering to the mammal a therapeutically effective amount of a neurodegenerative disease drug selected from the group consisting of: ciliary neurotrophic factor; cobalamin; coenzyme Q; Hepatocyte Growth Factor ("HGF"); N-acetylcysteine; nordihydroguaiaretic acid ("NDGA"); vascular endothelial growth factor ("VEGF"); benzyloxycarbonyl-Val-Ala-Asp(Ome)-fluoromethylketone ("zVAD-fmk"); and mixtures thereof, further administering a therapeutically effective amount of an ABC transporter inhibitor.

2. The method of claim 1, wherein the neurodegenerative disease comprises amyotrophic lateral sclerosis.

3. The method of claim 1, wherein the ABC transporter comprises at least one selected from the group consisting of P-glycoprotein ("P-gp") and Breast Cancer Resistance Protein ("BRCP").

4. The method of claim 1, wherein the inhibitor comprises at least one selected from the group consisting of elacridar; tariquidar; zosuquidar; (E)-4,4'-(2-(4-(3-ethoxyprop-1-en-1-yl)phenyl)-1H-imidazol e-4,5-diyl)bis(N-isopropylaniline) ("ONT-093"); laniquidar; a salt or solvate thereof, and mixtures thereof.

5. The method of claim 1, wherein at least one selected from the group consisting of the drug and inhibitor is part of a pharmaceutical composition.

6. The method of claim 5, wherein the pharmaceutical composition comprises an extended-release formulation.

7. The method of claim 1, wherein the drug and the inhibitor are co-administered to the mammal.

8. The method of claim 7, wherein the drug and the inhibitor are coformulated.

9. The method of claim 1, further comprising a step of detecting at least one symptom of the neurodegenerative disease and wherein administration of the drug and the inhibitor to the mammal takes place at the time or after the detection of mammal develops at least one symptom of the neurodegenerative disease.

10. The method of claim 1, further comprising detecting the concentration of the drug from the spinal cord, wherein the mammal that is administered the drug and the inhibitor has a higher spinal cord concentration of the drug than a mammal that is administered the drug only.

11. The method of claim 1, further comprising detecting the compound muscle action potential peak amplitude from said patient, wherein the mammal that is administered the drug and the inhibitor has a higher compound muscle action potential peak amplitude than a mammal that is administered the drug only.

12. The method of claim 1, wherein the mammal that is administered the drug and the inhibitor has improved survival as compared to a mammal that is administered the drug only.

13. The method of claim 1, wherein the mammal that is administered the drug and the inhibitor has delayed disease progression as compared to a mammal that is administered the drug only.

14. The method of claim 1, wherein the mammal is a rodent or a primate.

15. The method of claim 14, wherein the primate is a human.

16. The method of claim 1, wherein the drug is administered to the mammal by at least one route selected from the group consisting of inhalational, oral, rectal, vaginal, parenteral, topical, transdermal, pulmonary, intranasal, buccal, sublingual, ophthalmic, intrathecal, intravenous and intragastrical.

* * * * *

UNITED STATES PATENT AND TRADEMARK OFFICE
CERTIFICATE OF CORRECTION

PATENT NO. : 11,369,596 B2
APPLICATION NO. : 16/289273
DATED : June 28, 2022
INVENTOR(S) : Davide Trotti, Piera Pasinelli and Michael R. Jablonski Page 1 of 1

It is certified that error appears in the above-identified patent and that said Letters Patent is hereby corrected as shown below:

In the Specification

On Column 1, Lines 18-25, please replace the paragraph entitled "STATEMENT REGARDING FEDERALLY SPONSORED RESEARCH OR DEVELOPMENT" with the following paragraph:

--STATEMENT REGARDING FEDERALLY SPONSORED RESEARCH OR DEVELOPMENT
This invention was made with government support under W81XWH-11-1-0767 awarded by the Defense Health Agency, Medical Research and Development Branch, and NS074886 awarded by the National Institutes of Health. The government has certain rights in the invention.--

Signed and Sealed this
Eleventh Day of February, 2025

Coke Morgan Stewart
*Acting Director of the United States Patent and Trademark Office*